(12) United States Patent
Dewaele

(10) Patent No.: US 7,394,946 B2
(45) Date of Patent: Jul. 1, 2008

(54) METHOD FOR AUTOMATICALLY MAPPING OF GEOMETRIC OBJECTS IN DIGITAL MEDICAL IMAGES

(75) Inventor: Piet Dewaele, St. Niklaas (BE)

(73) Assignee: Agfa Healthcare, Mortsel (BE)

( * ) Notice: Subject to any disclaimer, the term of this patent is extended or adjusted under 35 U.S.C. 154(b) by 472 days.

(21) Appl. No.: 11/130,285

(22) Filed: May 16, 2005

(65) Prior Publication Data

US 2005/0259882 A1 Nov. 24, 2005

Related U.S. Application Data

(60) Provisional application No. 60/582,335, filed on Jun. 22, 2004.

(30) Foreign Application Priority Data

May 18, 2004 (EP) .................................. 04076454

(51) Int. Cl.
 G06K 9/36 (2006.01)
 G09G 5/00 (2006.01)
 H04N 9/74 (2006.01)
(52) U.S. Cl. ...................... 382/276; 382/128; 345/619; 348/580
(58) Field of Classification Search ....................... None
 See application file for complete search history.

(56) References Cited

U.S. PATENT DOCUMENTS 5,807,256 A 9/1998 Taguchi et al.

2003/0194057 A1 10/2003 Dewaele

FOREIGN PATENT DOCUMENTS

| CA | 20 50 561 A1 | 3/1992 |
|----|----|----|
| EP | 0 616 290 A2 | 9/1994 |
| EP | 1 293 925 A1 | 3/2003 |
| EP | 1 349 098 A1 | 10/2003 |
| WO | WO 91 11147 A1 | 8/1991 |
| WO | WO 01 55965 A2 | 8/2001 |

OTHER PUBLICATIONS

Chen C.C. et al., *Semi-Automatic Tool for Aligning a Parameterized CAD Model to Stereo Image Pairs*, vol. E82-D No. 12, 1582-1588 (Dec. 1999).
Johnson et al., Consistent Landmark and Intensity-Based Image Registration, vol. 21, 450-461 (May 2002).
Search report for EP 02 10 0307 (Jun. 26, 2002).
Search report for EP 04 07 6454 (Sep. 29, 2004).
Smyth P.P. et al., *Vertebral Shape: Automatic Measurement with Active Shape Models*, vol. 211, No. 2, pp. 571-578 (1999).
The Math Works, Image Processing Toolbox for Use With MATLAB, User's Guide, Version 3, pp. 5-2 to 5-32 (Jun. 2001).

*Primary Examiner*—Charles Kim
(74) *Attorney, Agent, or Firm*—Leydig Voit & Mayer, Ltd.

(57) ABSTRACT

A method of mapping geometrical objects to a digital image. At least one anchor point in a model is selected and mapped to the digital image. A geometric transformation is computed on the basis of at least one correspondence between an anchor object and a corresponding mapped object, and the calculated geometric transformation is applied to at least one geometric object thereby mapping it from the model image to a corresponding mapped position in the digital image.

8 Claims, 9 Drawing Sheets

Fig. 5 (b). RUS (Radius, Ulna, Short Bones) Regions of Interest
Distal Radius and Ulna Regions of Interest
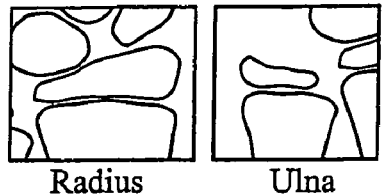
Radius    Ulna
Metacarpal Regions of Interest
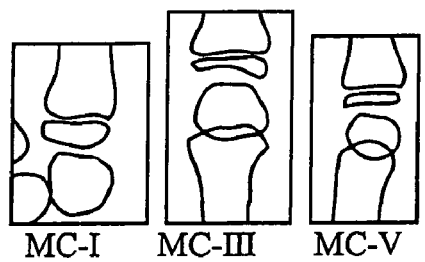
MC-I    MC-III    MC-V
Proximal Phalanx Regions of Interest
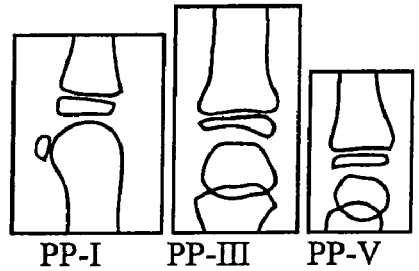
PP-I    PP-III    PP-V
Middle Phalanx Regions of Interest
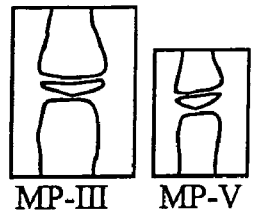
MP-III    MP-V
Distal Phalanx Regions of Interest
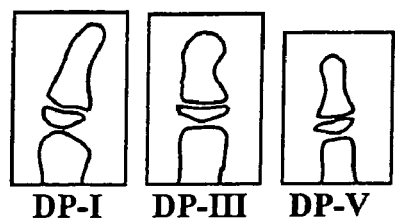
DP-I    DP-III    DP-V Fig. 5 (c). Carpal Regions Of Interest
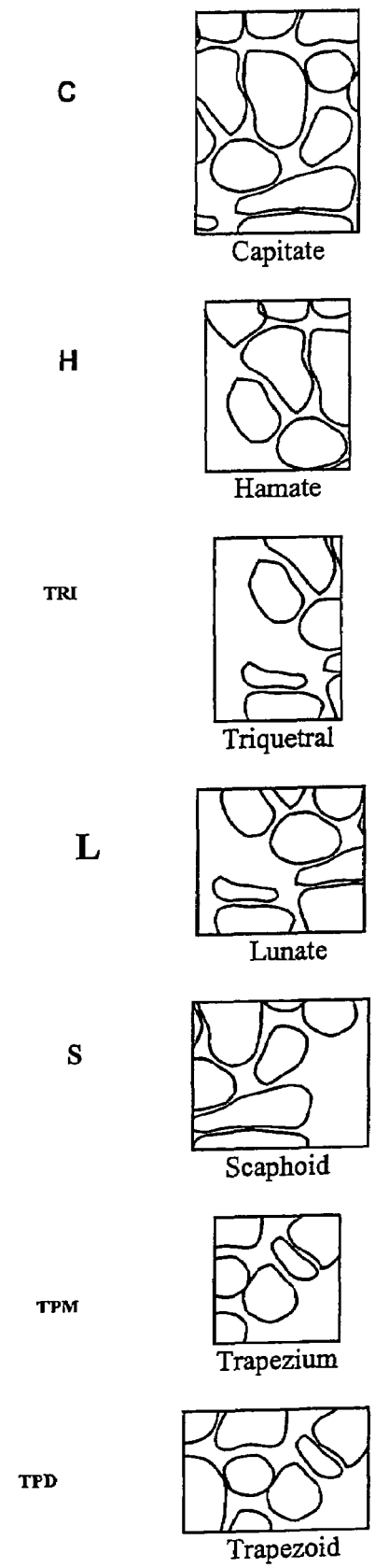

METHOD FOR AUTOMATICALLY MAPPING OF GEOMETRIC OBJECTS IN DIGITAL MEDICAL IMAGES

This application claims the benefit of U.S. provisional application No. 60/582,335, filed Jun. 22, 2004, which is incorporated by reference.

FIELD OF THE INVENTION

The present invention relates to computer-assisted method to map geometric objects in a digital medical image.

BACKGROUND OF THE INVENTION

In radiological practice, the radiographer frequently needs to locate specific anatomic structures on the radiograph in order to focus his attention on these specific image areas. The position of the image areas will typically depend on the examination type of the radiograph and the suspected disease; hence these locations are examination and diagnosis-specific.

For example, in bone age assessment according to the Tanner-Whitehouse method, 20 bony regions of interest (ROI) need be located on a hand radiograph, and staged against a set of reference stages depicted in an atlas. In European patent application EP A 1 293 925, a method is disclosed to automate the staging and scoring of these skeletal sites. The associated ROI of these sites is extracted and compared against a set of reference pictures and diagrams by presenting a given ROI simultaneously in close vicinity with its reference set. The location process for each of these regions of interest must be performed irrespective of the position of the hand itself in the image. A typical exposure error introducing positional variation is that the hand axis is placed in a rotated fashion with respect to the cassette borders of a cassette conveying a radiation detector such as a photo-stimulable phosphor screen on which the radiation image is recorded. Furthermore, irregular finger spread of fingers adds a second degree of rotational variation in the location of these ROI's. Hence, there is a need to enhance the location and extraction process of ROIs in a medical image.

A further location determination task in the Tanner and Whitehouse scoring method is that anatomic bony features are compared against geometric objects in relationship to anatomy. For example, in the scoring of the scaphoid, the stages G and H are characterized in that the direction of the lunate border of the scaphoid is compared with respect to the midline of the capitate. Therefore, the radiographer must continuously mentally map the capitate midline into the image in order to verify this feature and assign the correct stage to the scaphoid. Hence, there is a need to map this diagnostic line into the actual image, so as to avoid the need of continuous mental relocation.

A second diagnostic activity where objects need be located in an image is the field of geometric measurements. Obviously, in the film-based measurements, no assistance is offered in drawing the geometric objects or entities in the image. In European patent application EP A 1 349 098 a method is disclosed to automate the measurements in digitally acquired medical images by grouping measurement objects and entities into a computerized measurement scheme consisting of a bi-directionally linked external graphical model and an internal informatics model. In a measurement session according to European patent application EP A 1 349 098, a measurement scheme is retrieved from the computer and activated. Measurements are subsequently performed on the displayed image under guidance of the activated measurement scheme.

In this computerized method, a multitude of geometric objects must be mapped in the digital image onto which other measurement objects and finally measurement entities (such as distances and angles) are based. The basic geometric objects are typically key user points, which define other geometric objects onto which measurements are based. For example, two pairs of key points each define a line, and an angle between the resulting line pair, representing the angulation between anatomic structures, is computed. These key user points must be mapped in the image onto their corresponding anatomical landmark positions. In order to facilitate the initial position of these key user points, their position may be computed on the basis of a small number of anchor points, which are also defined in relationship with anatomy and will typically coincide with easily discernible anatomical landmarks.

A further location task when performing measurements in digital images is related to the selection of the image area and the proper resolution of the image for placing the geometrical objects such as measurement points. For large images of which only a downscaled version is displayed, the radiographer will usually prefer to position the key user points in the original image in order to use the full resolution for better positional accuracy of the key user points. Therefore, the image area around each sequential key user point must be displayed in its original resolution, which requires that the user first select the image area to be magnified. This is typically done by methods of the prior art by an additional mouse click in the image in the vicinity of the desired key user point, upon which the image is displayed at full resolution, or by panning in a second image window displaying the image at full resolution until the region around the desired key user point is viewed. However, the drawback of this manner of operation is that when the number of key user points is large, which is typically the case for complex measurement schemes, a large number of mouse manipulations is needed, hence this method is slow, fatiguing and error prone.

A third area in radiological operation that also requires a geometric location is that of quality assurance and quality control by means of an analyzing phantom. For example, in mammographic system quality control, a phantom with a specific spatial arrangement of geometric structures is used. These structures such as disk and bars serve to determine the image contrast and compare it against perceptibility thresholds. Geometric accuracy may be checked by measuring the structures' spatial locations in the image and compare them with their model counterpart. To automate the analysis of the imaged phantom, a CAD model may be used to reference the geometric structures against a coordinate reference system. This reference system may be established by means of small number of control points of known location. For these control points are part of the phantom, they are imaged simultaneously with the analyzing objects. By locating their position in the image, a correspondence between model and actual image can be established. After establishing the geometric transformation and performing the mapping of the model structures, as will be detailed in the sequel, the initial position of all referenced objects is easily found back in the image, and subsequent quality parameters are computed.

In EP 1 349 098 a method has been described for performing geometric measurements on digital radiographic images using graphical templates.

A digital image representation of a radiological image displayed. A measurement template comprising the set of measurement points or areas is displayed adjacent to the digital image. The measurement points or objects are mapped onto the displayed image by manually indicating locations of points in the displayed image corresponding with the points or objects of the template, and the co-ordinates of the resultant mapped points are stored and used for performing measurements on the displayed image. The described method is performed manually.

SUMMARY OF THE INVENTION

To overcome the drawbacks of the prior art the present invention provides a method as set out in the claims.

The present invention discloses a model-based geometric mapping method. In particular, geometric objects that need to be mapped in an image are encoded relative to a set of model anchor geometric objects, which in the preferred embodiment are key user points. The user manually maps the model anchor objects in the image, the number of which is typically very small. A geometric mapping transformation is subsequently established between the model anchor objects and the user-mapped model anchor objects. Subsequently, all geometric objects that need to be mapped in the image and that are specified within a coordinate system defined by the mapping model anchor objects, are automatically positioned in the target image, by applying the computed geometric transformation to the objects' defining parameters. Finally all mapped objects are rendered in the target image according to the values of their defining parameters.

Characteristics of Model Anchor Objects

The characteristics of model anchor objects can be enumerated as follows:

- Although any object may be used as a model anchor objects to which the geometric objects are defined, the model anchor objects will typically be easy to position, hence their defining number of degrees of freedom will be small. The number of degrees of freedom (d.o.f.) is the number of independent position variables that have to be specified in order to locate all parts of an object. Eligible anchor objects are for example anchor points (2 d.o.f. (displacement in x and y direction)), anchor lines (4 (two points) −2 (each point must lie on the line)=2 d.o.f.), and anchor circles (6−3=3 d.o.f. (center point coordinates and radius).
- A further characteristic of the model anchor objects is that their number will typically be small, but sufficient to enable accurate positioning of the geometrical objects. More anchor objects than needed to derive the geometric transform may be selected when they are considered topologically relevant. In that case, an over-determined solution is derived that fits a geometric transformation by minimizing e.g. a least-squares criterion.
- The type of image locations that model anchor objects represent can either be natural or artificial landmark entities. Natural anchor objects are typical, radiological well-manifested diagnostic positions, or reference lines in the image. Artificial landmark entities comprise specifically designed markers introduced in the radiographed subject or man-made objects such as prosthesis shapes.

Examples of Anchor Objects

Examples of suitable anchor point objects in radiographic images of a full-leg examination are e.g. the tip of the greater trochanter, the midpoint of the knee joint, the midpoint of the ankle joint.

Examples of suitable anchor line objects in radiographic images of the pelvis are e.g.

- the horizontal line connecting the iliac crest top points. For the iliac crest has circular sagittal cross sectional shape, its radiographic position is less affected by pelvic tilt.
- the topmost, bottommost horizontals, tangent to the obturator foramina,
- the leftmost and rightmost verticals, tangent to the obturator foramina,
- the line connecting both inferior rami of the pubis
- the ilioischial line (Kohler's line). Anatomically the superior ilioischial line is formed by the broad cortical surface of the siciatic notch (which lies posterior to the acetabular floor), and the inferior ilioischial line is formed by the cortical surface of the anterior ischium (anatomically this line does not correspond to the acetabular floor).
- the line connecting left and right teardrop. The true floor of the acetabulum corresponds to the radiographic teardrop. The teardrop lies in the inferomedial portion of the acetabulum, just above the obturator foramen. The lateral and medial lips correspond to the external and internal walls, respectively. The medial wall is a relatively constant radiographic finding and is not significantly distorted by small degrees of rotation, unlike the ilioischial line (Kohler's line), which may sometimes not consistenly represent the true acetabular floor (on straight AP radiographs, the ilioischial line will overlie the acetabular floor, but with an amount of rotation, this relationship may not be met)

Each of these lines is actually a 3D line, which projects as a line in a two-dimensional image. To the extent that the lines intersect in three dimensions, the representation as a set of (intersecting) anchor points may be used instead of a set of anchor lines.

Coordinate Frames in Model and Target Image (FIG. 1)

In the following explanation, a number of coordinate systems are used.

Let the model resp. target image coordinate system be defined as (u,v) resp. (x,y), with the x axis running from top to bottom (that is having rows as the running coordinate) and the y axis running from left to right (having columns as the running coordinate). U and v axis resp. x and y axis form a right-handed coordinate system, with positive angles departing from the u (resp. x) axis in the counterclockwise direction towards the v (resp. y) axis.

The anchor objects in the model (resp. target) image define a local second coordinate system (u',v') resp. (x',y'), into which the objects are encoded relatively. For example, when a set of anchor points is used for the model, the directional line segment from the first point of the set towards the second point of the set defines the x' axis. The perpendicular y' axis points positively in a direction such that both axes jointly form a right-handed coordinate system.

A third coordinate frame (u",v") resp. (x",y") may further be attached to the geometric object in the model resp. target image to describe the location of its constituent parts. For example, a coordinate system may be attached to a ROI to describe the pixels' position inside the ROI, in a way similar to the image coordinate system that describes the pixels' position in the original image. The defining parameters of the ROI's coordinate system are the location of its origin in the (u',v') resp. (x',y') coordinate system and the angle of its positive u" resp. x"axis with respect to the positive u' resp. x' axis. The direction of the positive v" resp. y"axis is then established so that the u" and v" respectively x" and y" axes jointly form a right-handed coordinate system.

DETAILED DESCRIPTION OF THE INVENTION

Figure 1:
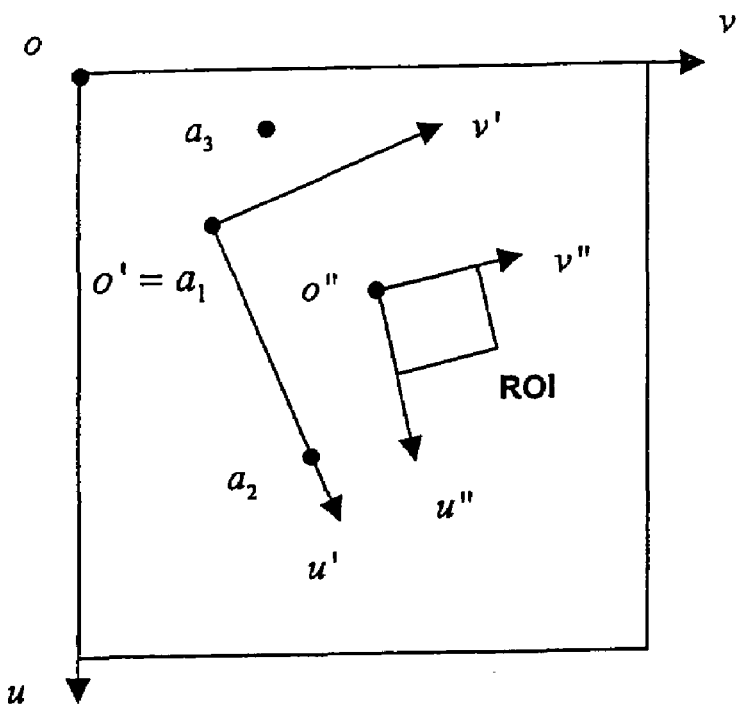
FIG. 1. Coordinate systems used in the context of the present invention: (a) model coordinate and (b) target coordinate systems: image coordinate systems u,v resp. x,y, anchor point and mapped anchor point coordinate systems u',v' resp. x',y', and ROI and mapped ROI coordinate systems u",v" resp. x",y".
Figure 1:
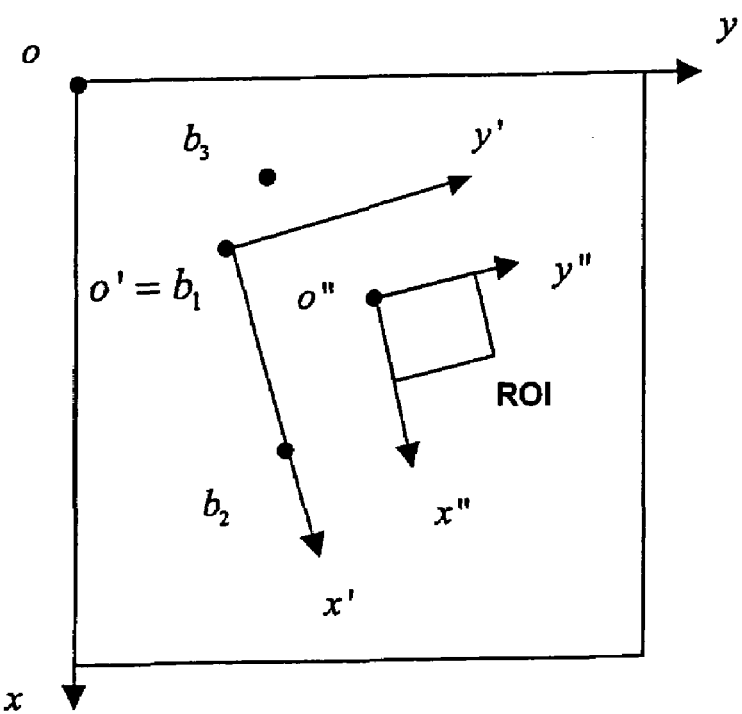

The geometric mappings that are considered in the context of the present invention can be classified in either linear mapping functions or non-linear mappings such as bilinear mappings, polynomial mappings and thin-plate spline mappings. These mappings are detailed along with the computation of them by means of correspondences between model anchor objects and image-mapped anchor objects. Special important cases are indicated. Decomposition of linear mappings is derived to be used in relative mappings, that use the full established transformation matrix, and absolute mappings, that use a reduced transformation matrix by omitting one or more components that are obtained by decomposition of the full transformation matrix. Next the encoding of geometric objects in the model anchor coordinate system is described. Finally, the result of applying the computed transformation or reduced transformation to specific geometric objects is derived.

1. Geometric Mapping Transforms

1.1 Linear Mapping Functions

This class of spatial 2D mapping can be expressed in terms of the general linear homogeneous 3×3 transformation matrix T and is commonly referred to as a homography. This transformation handles scaling, shearing, rotation, reflection, translation and perspective in 2D. A 4×4 transformation matrix in homogeneous coordinates similarly expresses the class of spatial 3D mappings. Without loss of generality, the third dimension is ignored in derivations, and the 2D object mappings only are considered in the sequel (that is mappings between the image xy and model uv coordinate systems). Coordinate systems are typically right-handed, in that the x axis is running from top to bottom (running inside a column), y axis running from left to right (running inside a row); xy forming a right-handed coordinate system.

$$T = \begin{bmatrix} a_{11} & a_{12} & a_{13} \\ a_{21} & a_{22} & a_{23} \\ a_{31} & a_{32} & a_{33} \end{bmatrix}, \begin{bmatrix} X \\ Y \\ 1 \end{bmatrix} = T \begin{bmatrix} U \\ V \\ 1 \end{bmatrix}$$

wherein the homogeneous coordinates have been normalized to have w=1. The uv coordinates denote model position; the xy coordinates denote image position. The homogeneous notation has the advantage that a translation is modeled as a matrix multiplication instead of requiring an additional vector addition, hence it may be encoded and computed simultaneously with the rotation and scaling components in dedicated hardware.

The 3×3 transformation matrix can best be understood by partitioning it into four separate sections. The 2×2 sub-matrix $$\begin{bmatrix} a_{11} & a_{12} \\ a_{21} & a_{22} \end{bmatrix}$$

specifies a linear transformation for scaling, shearing and rotation. The 2×1 sub-matrix $$\begin{bmatrix} a_{13} \\ a_{23} \end{bmatrix}$$

specifies a translation and the 1×2 sub-matrix $[a_{31}\ a_{32}]$ produces a perspective transformation. The element $[a_{33}]$ is responsible for overall scaling.

Linear mapping functions in 3D are represented by the 4×4 homogeneous matrix multiplication $$T = \begin{pmatrix} a_{11} & a_{12} & a_{13} & a_{14} \\ a_{21} & a_{22} & a_{23} & a_{24} \\ a_{31} & a_{32} & a_{33} & a_{34} \\ a_{41} & a_{42} & a_{43} & a_{44} \end{pmatrix}, \begin{bmatrix} X \\ Y \\ Z \\ 1 \end{bmatrix} = T \begin{bmatrix} U \\ V \\ W \\ 1 \end{bmatrix}.$$

In a similar way, the 3×4 sub-matrix $$\begin{pmatrix} a_{11} & a_{12} & a_{13} & a_{14} \\ a_{21} & a_{22} & a_{23} & a_{24} \\ a_{31} & a_{32} & a_{33} & a_{34} \end{pmatrix}$$

represents the affine component (rotations, translations, shearings), the 1×3 sub-matrix $(a_{41}\ a_{42}\ a_{43})$ represents the projectivities and the coefficient $a_{44}$ is responsible for overall scaling for homography mappings in 3D.

The matrix T specifies the forward mapping functions X and Y that transform model source input images in the (u,v) coordinate system onto target output images in the (x,y) coordinate system. A similar transformation applies to the inverse mapping functions U and V to map the target image into the input image.

Special Cases of Linear Mappings

Euclidean and Euclidean Similarity Mapping and Similarity Reflection

Euclidean mappings offer four degrees of freedom, in the case of isotropic scaling, and are able to map a bounded line segment into a bounded line segment (with different lengths and orientations). These mappings are also termed rigid body transformations in that they leave the shape of the transformed objects similar up to a scaling factor. A rigid body transformation consists of a composition of a rotation about the origin over an angle $\theta$ w.r.t. the u-axis in the counterclockwise direction, a translation $(T_u, T_v)$ w.r.t. the origin and scale factors $S_u, S_v$ applied to the coordinates u and v:

$$T_E = \begin{pmatrix} \cos\theta & -\sin\theta & 0 \\ \sin\theta & \cos\theta & 0 \\ 0 & 0 & 1 \end{pmatrix} \begin{pmatrix} 1 & 0 & T_u \\ 0 & 1 & T_v \\ 0 & 0 & 1 \end{pmatrix} \begin{pmatrix} S_u & 0 & 0 \\ 0 & S_v & 0 \\ 0 & 0 & 1 \end{pmatrix}$$

Scaling T to have a non-unity term $a_{33}$ can reduce the 5 variables in this mapping to 4.

Considering isotropic scaling by a factor S, the combined Euclidean mapping can be written as $$T_E = \begin{pmatrix} S\cos\theta & \sin\theta & T_u \\ -\sin\theta & S\cos\theta & T_v \\ 0 & 0 & 1 \end{pmatrix}$$

The Euclidean similarity reflection mapping is obtained by concatenating this matrix with a reflection matrix. For example, reflection around the u-axis resp. v-axis are represented by the matrices $$T_{F_x} = \begin{pmatrix} 1 & 0 & 0 \\ 0 & -1 & 0 \\ 0 & 0 & 1 \end{pmatrix}, T_{F_y} = \begin{pmatrix} -1 & 0 & 0 \\ 0 & 1 & 0 \\ 0 & 0 & 1 \end{pmatrix}$$

In three dimensions, a rigid body transformation is characterized by six degrees of freedom (three translation components and three rotations around each of the image axes)

$$T_E = \begin{pmatrix} \cos\theta_w & -\sin\theta_w & 0 & 0 \\ \sin\theta_w & \cos\theta_w & 0 & 0 \\ 0 & 0 & 1 & 0 \\ 0 & 0 & 0 & 1 \end{pmatrix} \begin{pmatrix} 1 & 0 & 0 & 0 \\ 0 & \cos\theta_u & -\sin\theta_u & 0 \\ 0 & \sin\theta_u & \cos\theta_u & 0 \\ 0 & 0 & 0 & 1 \end{pmatrix}$$

$$\begin{pmatrix} \cos\theta_v & 0 & \sin\theta_v & 0 \\ 0 & 1 & 0 & 0 \\ -\sin\theta_v & 0 & \cos\theta_v & 0 \\ 0 & 0 & 0 & 1 \end{pmatrix} \begin{pmatrix} 1 & 0 & 0 & T_u \\ 0 & 1 & 0 & T_v \\ 0 & 0 & 1 & T_w \\ 0 & 0 & 0 & 1 \end{pmatrix}$$

The first matrix represents a rotation in the counterclockwise direction around the w-axis, the second and third likewise represent rotation around the u- and v-axis respectively. The angles of rotation are the so-called Euler angles. The fourth matrix represents three-dimensional translation.

Affine Mapping

The general representation of an affine transformation is $$T_A = \begin{bmatrix} a_{11} & a_{12} & a_{13} \\ a_{21} & a_{22} & a_{23} \\ 0 & 0 & 1 \end{bmatrix}$$

Division by the homogeneous coordinate w' is avoided by selecting w=w'=1. The affine mapping corresponds to an orthographic or parallel plane projection from the source plane (u,v) onto the target plane (x,y).

Affine mappings in 2D offer six degrees of freedom, and are able to map a triangle (three non-collinear points) into a triangle. An input rectangle can be mapped into a parallelogram at the output. Affine mappings result from applying non-zero off-diagonal terms in the scaling matrix. Considering the case where $a_{11}=a_{22}=1$ and $a_{21}=0$. By making a $a_{12}\neq 0$, x is made linearly dependent on u and v, while y remains identical to v. This operation results in shearing a rectangle, with sides parallel to the u and v axes, along the u coordinate axis into a parallelogram in the (x,y) coordinate system. The side pair that was originally parallel to the v axis is now oblique w.r.t. the y axis. A similar non-zero coefficient $a_{21}\neq 0$ results in a shearing parallel to the coordinate axis. The general form of an affine mapping may therefore also be written in decomposed form as $$T_A = T_E \begin{pmatrix} 1 & s_u & 0 \\ 0 & 1 & 0 \\ 0 & 0 & 1 \end{pmatrix} \begin{pmatrix} 1 & 0 & 0 \\ s_v & 1 & 0 \\ 0 & 0 & 1 \end{pmatrix}$$

The inverse of an affine mapping is itself affine, and is computed from the inverse $T_A^{-1} = \text{adj}(T_A)/\det(T_A)$.

In three dimensions, each new coordinate is a linear combination of all three, and the shearing operations geometrically result in transforming a cube or rectangular volume into a parallelepiped.

Projective Mapping

A projective mapping is able to describe object transformations obtained through perspective projections onto the viewing, projection or detector plane. In general the coefficients $[a_{31}\ a_{32}]$ are nonzero, and hence a projective mapping offers eight degrees of freedom.

$$\begin{bmatrix} x' \\ y' \\ w' \end{bmatrix} = T\begin{bmatrix} u \\ v \\ w \end{bmatrix} = \begin{bmatrix} a_{11} & a_{12} & a_{13} \\ a_{21} & a_{22} & a_{23} \\ a_{31} & a_{32} & a_{33} \end{bmatrix}\begin{bmatrix} u \\ v \\ w \end{bmatrix} \text{ where } x = x'/w' \text{ and } y = y'/w'.$$

Projective mappings preserve lines in all orientations. That is, lines map into lines (although not of the same orientation). In contrast to affine mappings, projective mappings offer eight degrees of freedom, and are able to map a planar quadrilateral into a planar quadrilateral.

Perspective transformations preserve parallel lines only when they are parallel to the projection plane. Otherwise lines converge to a vanishing point.

The forward mapping functions of a projective mapping are obtained by dividing by the homogeneous coordinate w'

$$X(u, v) = x = \frac{x'}{w'} = \frac{a_{11}u + a_{12}v + a_{13}}{a_{31}u + a_{32}v + a_{33}}$$

$$Y(u, v) = y = \frac{y'}{w'} = \frac{a_{21}u + a_{22}v + a_{23}}{a_{31}u + a_{32}v + a_{33}}$$

The inverse of a projective mapping is itself projective, and is computed from the inverse $T_P^{-1} = \mathrm{adj}(T_P)/\det(T_P)$ The projective mapping may by used to calibrate an image such that measurements can be performed metrically in the mapped image. The points may be landmarks at a certain plane, possibly rotated around is the x and y axis, at a certain depth in the patient. The mapping may also be used to bring two planes of two images taken at two different times into metrical correspondence, i.e. distances in the mapped plane may be calculated in an Euclidean way and compared without any further conversion.

Computation of the Linear Mapping Function

Euclidean Case

The matrix $T_E$ holds only 4 unknowns and can be written as $$T_E = \begin{pmatrix} a & b & c \\ -b & a & f \\ 0 & 0 & 1 \end{pmatrix}$$

The coefficients can be determined by establishing a correspondence between two points in the model image and target image. Let $(u_k, v_k)$ resp. $(x_k, y_k)$, k=0,1 be two points (e.g. endpoints of a line segment) in the model image resp. target image. Each pair of corresponding point generates two equations in the unknown coefficients by rewriting the equations X(u,v) resp. Y(u,v) as follows:

$au_k + bv_k + c = x_k$ $-bu_k + av_k + f = y_k$, k=0,1

Written in matrix notation, $$\begin{bmatrix} u_0 & v_0 & 1 & 0 \\ u_1 & v_1 & 1 & 0 \\ v_0 & -u_0 & 0 & 1 \\ v_1 & -u_1 & 0 & 1 \end{bmatrix} \begin{bmatrix} a \\ b \\ c \\ f \end{bmatrix} = \begin{bmatrix} x_0 \\ x_1 \\ y_0 \\ y_1 \end{bmatrix}$$

This system of equations is solved by linear system solvers known in the prior art. The coefficients may now be equated to the coefficients of $T_E$ written in terms of the concatenated elementary geometric operations to determine constituent components of translation, scaling and rotation:

$T_u = C$ $T_v = f$ $S = \sqrt{a^2 + b^2}$ $\theta = \arccos(a/S)$

In three dimensions, a rigid body transformation has 6 degrees of freedom, requires at least two point correspondences to establish it.

Affine Case

The matrix $T_A$ holds only 6 unknowns 6 (6 degrees of freedom) that can be determined by establishing a correspondence between at least three non-co-linear points in the model image and target image. Let $(u_k, v_k)$ resp. $(x_k, y_k)$, k=0,1,2 be three points (e.g. corner points of a triangle) in the model image resp. target image. Each pair of corresponding points generates two equations in the unknown coefficients by rewriting the equations X(u,v) resp. Y(u,v) as follows:

$au_k + bv_k + c = x_k$ $du_k + ev_k + f = y_k$, k=0 ... 2

Written in matrix notation, $$\begin{bmatrix} u_0 & v_0 & 1 & 0 & 0 & 0 \\ u_1 & v_1 & 1 & 0 & 0 & 0 \\ u_2 & v_2 & 1 & 0 & 0 & 0 \\ 0 & 0 & 0 & u_0 & v_0 & 1 \\ 0 & 0 & 0 & u_1 & v_1 & 1 \\ 0 & 0 & 0 & u_2 & v_2 & 1 \end{bmatrix} \begin{bmatrix} a \\ b \\ c \\ d \\ e \\ f \end{bmatrix} = \begin{bmatrix} x_0 \\ x_1 \\ x_2 \\ y_0 \\ y_1 \\ y_2 \end{bmatrix}$$

This system of equations is solved by linear system solvers known in the prior art.

In 3D, the affine transformation in homogeneous coordinates has 12 degrees of freedom, hence it requires at least 4 non-coplanar point correspondences (or 4 intersecting planes). Hence, these transformations in 3D are able to map a tetrahedron into a tetrahedron. A similar system of equations is established to determine the 12 coefficients.

The coefficients of the affine mapping are now equated to the coefficients of $T_A$ written in terms of the concatenated elementary geometric operations to determine constituent components of translation, scaling, rotation and shearing. It follows immediately that $T_u = C$ $T_v = f$ The determination of the scale S, the rotation $\theta$ in counter-clockwise direction and the shears $s_u$, $s_v$ can be retrieved from the coefficients a,b,d,e by first concatenating the individual matrices and then equating each of the members of the concatenated matrix to a,b,d,e respectively. The concatenated matrix is $$S \begin{bmatrix} \cos\theta & -\sin\theta \\ \sin\theta & \cos\theta \end{bmatrix} \begin{bmatrix} 1 & s_u \\ 0 & 1 \end{bmatrix}$$

$$\begin{bmatrix} 1 & 0 \\ s_v & 1 \end{bmatrix} = \begin{bmatrix} S\cos\theta & S(s_u\cos\theta - \sin\theta) \\ S\sin\theta & S(s_u\sin\theta + \cos\theta) \end{bmatrix} \begin{bmatrix} 1 & 0 \\ s_v & 1 \end{bmatrix} =$$

$$\begin{bmatrix} S\cos\theta + Ss_v(s_u\cos\theta - \sin\theta) & S(s_u\cos\theta - \sin\theta) \\ S\sin\theta + Ss_v(s_u\sin\theta + \cos\theta) & S(s_u\sin\theta + \cos\theta) \end{bmatrix} = \begin{bmatrix} a & b \\ d & e \end{bmatrix}$$

When the rotation is preceding the shearings, another matrix s results. This decomposition of the latter can be used to determine the elementary matrices corresponding to the reverse sequence. The advantage of decomposition is that selective components can be cancelled by substituting them by the unity matrix. For example, when the determinant of the transformation matrix of the 2×2 upper left matrix is not unity, or equivalently the matrix S in the singular value decomposition U·S·V' has non-zero off-diagonal elements, the transformation is not rigid body, which geometric property can be achieved by canceling the shearing component. Likewise, as will be apparent in the application of mapping ROI's, canceling the rotation component can be useful also, e.g. to have the mapped borders of the ROI staying parallel to the image borders in the transformed image. The decomposition according to the forward sequence of shearing followed by rotation is derived in the following.

The notation can be simplified by introducing the variables A and B defined as $S \cos \theta = A$ and $S \sin \theta = B$, yielding the following non-linear system of equations $$a = A + s_u s_v A - s_v B$$

$$b = s_u A - B$$

$$d = B + s_u s_v B + s_u A$$

$$e = s_u B + A$$

The solutions can be found by rewriting the factors $s_u, s_v, B$ as a function of A and the known coefficients a,b,d,e, solving for the roots of this function, and straightforwardly deriving the values for $s_u, s_v, B$ for all values of A.

Using some algebraic manipulation, the factors $s_u, s_v, B$ can be rewritten as $$s_u = \frac{1}{A}\left(b + \frac{bd - ae}{b}\right) + \frac{e}{b}$$

$$s_v = \frac{a}{b} - \frac{A}{b}$$

$$B = \frac{bd - ae}{b} + A\frac{e}{b}$$

Note that $ae - bd = \det(T_A) = D$. The quadratic equation in A then becomes $$(b^2 + e^2)A^2 - 2DeA + D(D - b^2) = 0$$

This equation has only real roots if the discriminant is positive, which leads to the conditions $D > 0$ and $(b^2 + e^2) > D$. The two roots are easily computed by the standard formula for roots of quadratic equations. For each value of A, the factors $s_u, s_v, B$ are obtained from their functions of A given above.

The equations may equally be rewritten with $s_u$ as the unknown, leading to the solution of a quadratic equation, which has a double root $$s_u = \pm\sqrt{\frac{b^2 + e^2}{D} - 1}$$

The same condition $(b^2 + e^2) > D$ is needed for the factor $s_u$ to have real values.

Obviously, the original matrix can be factorized in two ways. To reduce computations when the transformation $T_A$ is carried out by as sequence of consecutive shearings, that solution may be selected, which has zero coefficients for one of the shearings $s_u, s_v$. The selection of one of the two decompositions can be objectified by calculating how much the total of all individual components of rotation and shearing differ from the unity matrix, as this matrix represents the identity transform, implying no change of the model shape, apart from a translation. This is achieved by subtracting the identity matrix of each individual component of a decomposition (i.e. calculating $T_R - I$ with $T_R$ the rotational component for example), summing the absolute values of all elements of this difference matrix to yield an individual component's deviation measure, finally summing all deviation from unity measures of all components of a decomposition and selecting that decomposition which has the least overall deviation from unity measure. This novel strategy can further be complemented by removing small components, in the sense of deviation from the identity matrix just defined, by substituting them by the identity matrix, to achieve a simpler chain of elementary transformations, without sacrificing mapping accuracy of the resulting combined transformation.

In 3D, an affinity has 12 degrees of freedom, hence its solution can be derived from a minimum of 4 non-coplanar points, or equivalently using their dual of planes, by 4 non-coplanar planes (i.e. forming a tetrahedron).

Projective Case

The matrix T can be normalized so that $a_{33} = 1$, so that eight coefficients need be determined to infer a projective mapping from image data. These coefficients can be determined by establishing a correspondence between four points in the model image and target image. Let $(u_k, v_k)$ resp. $(x_k, y_k)$, $k = 0 \ldots 3$ be four points (e.g. corner points of a quadrangle) in the model image resp. target image. Each pair of corresponding points generates two equations in the unknown coefficients $a_{ij}$ by rewriting the equations $X(u,v)$ resp. $Y(u,v)$ as follows:

$$a_{11}u_k + a_{12}v_k + a_{13} - a_{31}u_k x_k - a_{32}v_k x_k = x_k$$

$$a_{21}u_k + a_{22}v_k + a_{23}a_{31}u_k y_k - a_{32}v_k y_k = y_k, k = 0 \ldots 3$$

Written in matrix notation, $$\begin{bmatrix} u_0 & v_0 & 1 & 0 & 0 & 0 & -u_0 x_0 & -v_0 x_0 \\ u_1 & v_1 & 1 & 0 & 0 & 0 & -u_1 x_1 & -v_1 x_1 \\ u_2 & v_2 & 1 & 0 & 0 & 0 & -u_2 x_2 & -v_2 x_2 \\ u_3 & v_3 & 1 & 0 & 0 & 0 & -u_3 x_3 & -v_3 x_3 \\ 0 & 0 & 0 & u_0 & v_0 & 1 & -u_0 y_0 & -v_0 y_0 \\ 0 & 0 & 0 & u_1 & v_1 & 1 & -u_1 y_1 & -v_1 y_1 \\ 0 & 0 & 0 & u_2 & v_2 & 1 & -u_2 y_2 & -v_2 y_2 \\ 0 & 0 & 0 & u_3 & v_3 & 1 & -u_3 y_3 & -v_3 y_3 \end{bmatrix} \begin{bmatrix} a_{11} \\ a_{12} \\ a_{13} \\ a_{21} \\ a_{22} \\ a_{23} \\ a_{31} \\ a_{32} \end{bmatrix} = \begin{bmatrix} x_0 \\ x_1 \\ x_2 \\ x_3 \\ y_0 \\ y_1 \\ y_2 \\ y_3 \end{bmatrix},$$

this is a linear system of the form $Ax = b$, that is solved by linear system solvers known in the prior art. These techniques rely for example on inverting the matrix A, so that the solution is found as $x = A^{-1}b$. This yields a solution to the general planar quadrilateral-to-quadrilateral mapping problem. Computational speedups are possible in the special cases of a quadrilateral to (unit) square mapping and the (unit) square to quadrilateral mapping. The general case of quadrilateral-to-quadrilateral mapping can also be speeded up by concatenating these special cases in cascade.

As points and lines are dual to each other in projective space, 4 non-collinear lines in 2D can alternatively determine the homography. Similarly, in 3D a homography has 15 degrees of freedom (the overall scaling can be set to unity without loss of generality), hence it is fully determined by a minimum of 5 points, or alternatively by 5 planes.

A projective transformation cannot be factored into elementary shearings along the u or v axis only. Instead, decomposition in a purely projective component and an affine component is considered. The purely projective component is able to transform converging lines that are originally parallel in the model but converge in the image towards the vanishing point for the line direction. The affine component accounts for global alignment and reduction of distortion along the axes. This decomposition is accomplished as follows.

Define $T=T_A T_P$ where $T_P$ is a purely projective transform, and $T_A$ an affine transform. Define the projective component as $$T_P = \begin{bmatrix} 1 & 0 & 0 \\ 0 & 1 & 0 \\ g & h & 1 \end{bmatrix}$$

Hence, the affine component is derived as $$T_A = TT_P^{-1} = \begin{bmatrix} a-cg & b-ch & c \\ d-fg & e-fh & f \\ 0 & 0 & 1 \end{bmatrix}$$

This affine matrix may further be decomposed into a rigid body transformation (scale, rotation and translation) and elementary shearing transformations as specified previously. As with the affine factorization, components that are small may be ignored without sacrificing positional accuracy of the mapped objects.

The foregoing detailed description of the linear mappings is needed to describe the application of a fast mapping of complete ROI's or image areas in the sequel.

Computation of the Linear Mapping Functions in the Over-Determined Case

When the model contains more anchor points than needed to specify a geometric transformation, then m>n, i.e. there are more equations than unknowns in the linear system $Ax=b$. For example, more than two model points may be selected to infer an Euclidean similarity transform. This problem is called over-determined, and generally no x satisfies $Ax=b$ exactly. The underdetermined problem, where m<n occurs less frequently and is generally unwanted because it would leave too much degrees of freedom. Three standard ways in the prior art are used to solve the least squares problem, all of them are based on matrix factorizations: the normal equations, the QR decomposition and the singular value decomposition (SVD).

1.2 Non-Linear Mapping Functions 1.2.1 Bilinear Mapping

A bilinear mapping is the tensor product of two affine functions of one variable each (coordinate variables u and v). Geometrically (FIG. 2), it means that an arbitrary point inside the unit model square ABCD is obtained by performing two linear interpolations. The one is obtained by interpolating on a pair of juxtaposed edges AD and BC using the same coordinate value u to divide the edge yielding points P and Q on AD and BC respectively. The other is obtained by interpolating the desired point on the line PQ using the other coordinate value v.

The tensor product is written as $T_B(u,v)=(X(u,v),Y(u,v))=(T_{B_x}(u,v),T_{B_y}(u,v))$, with $T_{B_x}(u,v), T_{B_y}(u,v)$ of the form $T_{B_x}(u,v)=(mu+n)(pv+q)=auv+bu+cv+d$ $T_{B_y}(u,v)=(m'u+n')(p'v+q')=euv+fu+gv+h$ The technique whereby each coordinate transformation $T_{B_x}(u,v), T_{B_y}(u,v)$ are bilinear functions is called a bilinear transformation, and the technique of using a bilinear transformation for the four-point mapping is called bilinear interpolation.

Computation of the Bilinear Mapping

Algebraic Determination of a Point Mapping

The 8 parameters a . . . d, a' . . . d' are determined by specifying the correspondences between $T_B(0,0)=A(x_0,y_0)$, $T_B(0,1)=B(x_1,y_1)$, $T_B(1,1)=C(x_2,y_2)$, $T_B(0,0)=D(x_3,y_3)$, or equivalently $T_{B_x}(0,0)=x_0$ $T_{B_x}(0,1)=x_1$ $T_{B_x}(1,1)=x_2$ $T_{B_x}(1,0)=x_3$ $T_{B_y}(0,1)=y_0$ $T_{B_y}(0,1)=y_1$ $T_{B_y}(1,1)=y_2$ $T_{B_y}(1,0)=y_3$ which leads to a system of 8 equations in the unknowns a . . . h, or equivalently, two systems of 4 equations in the unknowns a . . . d and e . . . h respectively.

The coordinate values (u,v) may also describe the position of a point object inside a non-square model quadrangle. This point is mapped to its corresponding position in a non-square target quadrangle, following the method outlined in the sequel. The transform goes between an intermediate unit square yielding intermediate bilinear coordinates of the point in the original quadrangle. Denoting with U,V the Cartesian coordinates of the corners of an input quadrangle, and denoting with I,J and X,Y the intermediate unit square coordinates ordered in clockwise direction starting from the origin and the output quadrangle Cartesian corner coordinates $U=[u_0 u_1 u_2 u_3]'$ $V=[u_0 u_1 u_2 u_3]'$ $I=[i_0 i_1 i_2 i_3]'=[0011]'$ $J=[j_0 j_1 j_2 j_3]'=[0110]'$ $X=[x_0 X_1 X_2 X_3]'$ $Y=[y_0 y_1 y_2 y_3]'$ Let (u,v) denote the Cartesian image coordinates of an input (model) point, let (i,j) denote the bilinear coordinates of the input point w.r.t. the input quadrangle, which are also the Cartesian coordinates in the intermediate unit square coordinate system, and let (x,y) denote the output Cartesian coordinates of the mapped input point now referenced w.r.t. the output quadrangle. The forward transform matrix that maps the unit square corner points into the target quadrangle's vertices is denoted by $$A = \begin{bmatrix} i_0 j_0 & i_0 & j_0 & 1 \\ i_1 j_1 & i_1 & j_1 & 1 \\ i_2 j_2 & i_2 & j_2 & 1 \\ i_3 j_3 & i_3 & j_3 & 1 \end{bmatrix}$$

The mapping is then determined following four steps (FIG. 2):

1. Compute the forward bilinear transform from the unit square towards the input quadrangle. The coefficients a . . . d and e . . . h are obtained by $[abcd] = A^{-1}U$ $[efgh] = A^{-1}V$ 2. Determine the inverse transform from the input quadrangle towards the intermediate unit square, enabling the computation of the bilinear coordinates of an input point referenced against the input quadrangle. This is performed by solving a quadratic equation for the value of j $c_2 j^2 + c_1 j + c_0 = 0$ with $c_2 = -ec + ga$ $c_1 a(h-v) + e(u-d) - fc + gb$ $c_0 = b(h-v) + f(u-d)$ This equation may have only one root when $c_2 = 0$. Otherwise two roots are obtained as $$j = \frac{-c_1 \pm \sqrt{c_1^2 - 4c_0 c_2}}{2c_2}$$

For each root determine the value of i as $$i = \frac{(u - cj - d)}{aj + b}.$$

One root is retained to yield a solution point (i,j) e.g. the point that lies inside the unit square when the input (model) point (u,v) lies inside the input (model) quadrangle. The solution does not exist when the discriminant $c_1^2 - 4c_0 c_2 < 0$. This region is bounded by the parabolic $c_1^2 - 4c_0 c_2 = 0$ in the u,v plane. The parabola is the envolutory of all transformed lines $u = u_0, u_0$ constant (vertical lines). These lines fold over, characterizing the existence of two solutions.

A similar derivation of the inverse solution could depart by determining i as the roots of a quadratic equation. The region for which no solution exists (discriminant less than zero) is implicitly bounded by the same parabola, and again two solutions exist as the tangent lines, representing transformed lines $v = v_0, v_0$ constant (horizontal lines).

3. Compute the forward bilinear transform from the unit square towards the output quadrangle. The coefficients a . . . d and e . . . h of this mapping are obtained by $[a'b'c'd'] = A^{-1}X$ $[e'f'g'h'] = A^{-1}Y$ 4. The bilinear coordinates (i,j) of the input point (u,v) are now mapped towards their Cartesian position (x,y) with respect to the output quadrangle by applying the forward transform $$x = \begin{bmatrix} ij & i & j & 1 \end{bmatrix} \begin{bmatrix} a' \\ b' \\ c' \\ d' \end{bmatrix}$$

$$y = \begin{bmatrix} ij & i & j & 1 \end{bmatrix} \begin{bmatrix} e' \\ f' \\ g' \\ h' \end{bmatrix}$$

Figure 2:
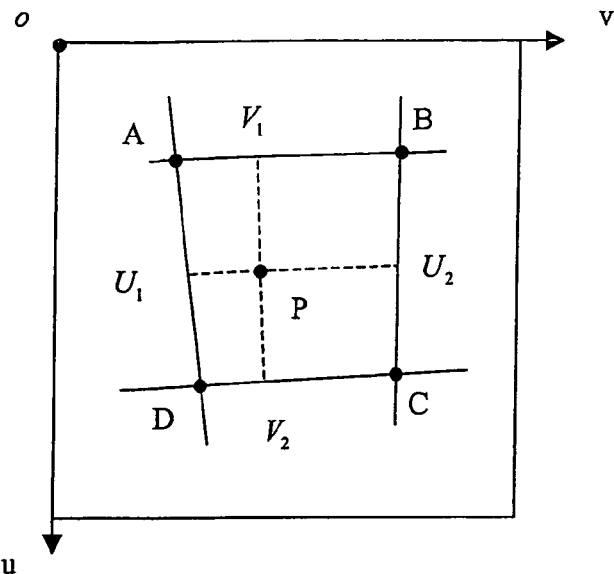
FIG. 2. Bilinear mapping of a point P referenced in a quadrangle ABCD to a point P' referenced in a quadrangle A'B' C'D'
Figure 2:
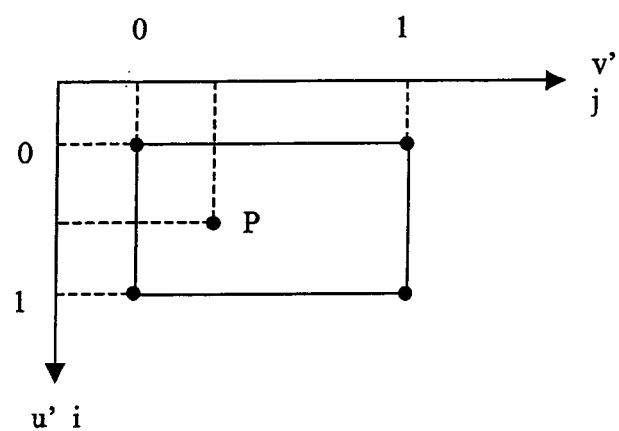
Figure 2:
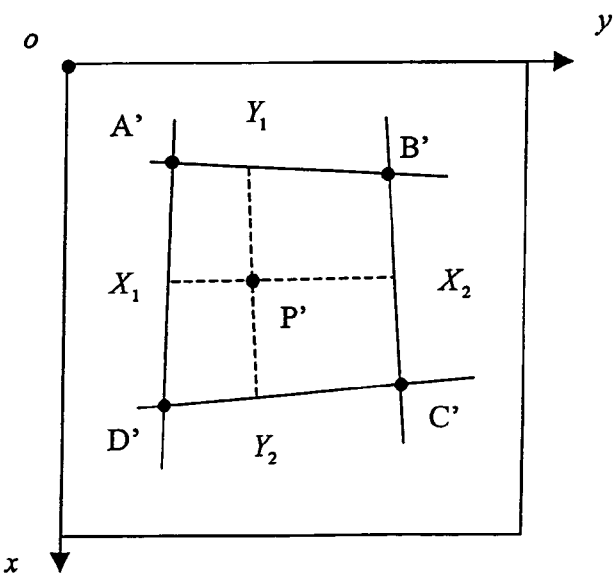

Alternatively, the position of the mapped point in the target image may be obtained by emulating the geometric construction according to FIG. 2 whereby the bilinear coordinate i divides a pair of juxtaposed quadrangle borders associated with the x axis to yield points $X_1$ and $X_2$, and the bilinear coordinate j divides a pair of juxtaposed quadrangle borders associated with the y axis to yield points $Y_1$ and $Y_2$. The mapped point is subsequently found as the intersection point between line $X_1 X_2$ and line $Y_1 Y_2$.

Point sets referenced w.r.t. the input quadrangle may be mapped to their associated point set in the output quadrangle by applying the transforms of the foregoing procedure to each point of the set. Other objects relying on points in their definition may be mapped likewise. Horizontal and vertical lines of the (u,v) plane are transformed into lines; however, other lines of the (u,v) plane are transformed into curves of second degree (parabolas). A uniform subdivision of the edges of the input unit square or input quadrangle is mapped onto a uniform subdivision of the edges of the output quadrilateral.

Geometric Determination of a Point Mapping

The first component consists in transposing the position of the point in the input quadrangle into a point in the intermediate unit square (of which the Cartesian coordinates are equal to the bilinear coordinates of the point). This point can be found as the intersection of two lines of constant bilinear coordinate i and j, each line being tangent to the parabola delineating the region in the u,v plane for which no inverse exists. The parabola is given by the equation $c_1^2 - 4c_0 c_2 < 0$, which is an equation in the variables u,v of the input model coordinate system, and the coefficients are solely dependent on the coordinates of the corner points of the model quadrilateral. For there are two solutions for each bilinear coordinate (four solutions for the (i,j) coordinates in total), that solution must be selected that has i,j coordinates between 0 and 1 when the input point lies inside the model quadrangle. The second component consists in determining the position of an arbitrary point with bilinear coordinates (i,j) of the unit square in the target quadrangle. This transposition can be found by two linear interpolations. As illustrated in FIG. 2, first the i coordinate is interpolated on the edges A'D' and B'C', obtaining points $X_1, X_2$ respectively. Next the j coordinate is interpolated on the line $X_1 X_2$, obtaining point p'. Alternatively, the j coordinate may be interpolated on the line A'B' and D'C', obtaining points $Y_1, Y_2$ respectively. The intersection of lines $X_1 X_2$ and $Y_1 Y_2$ also yields point P'.

The advantage of the bilinear mapping is that the four corner points need not lie in a single plane; hence they may represent anatomical landmarks lying at different non-coplanar depths in the patient. In contrast, the quadrilateral-to-quadrilateral projective mapping assumes the quadrangles' corner points all lie in the same physical plane.

1.2.2. Polynomial Mapping

A polynomial mapping is defined by a polynomial function of the form $$X(u, v) = x = \sum_{i=0}^{N} \sum_{j=0}^{N} a_{i,j} u^i v^j$$

$$Y(u, v) = y = \sum_{i=0}^{N} \sum_{j=0}^{N} b_{i,j} u^i v^j$$

The u,v variables are coordinates in the undistorted model, x,y are coordinates in the target image. N is the polynomial order, the $a_{ij}, b_{ij}$ are mapping coefficients that characterize the transformation. When N=1, the mapping reduces to the previously described bilinear transformation, for which four anchor-point correspondences need be established:

$$x = a_{00} + a_{10}u + a_{01}v + a_{11}uv$$

$$y = b_{00} + b_{10}u + b_{01}v + b_{11}uv$$

In general, the minimum number of anchor points needed is $(N+1)^2$ for a polynomial mapping of order N. When more anchor points are available, a pseudo-inverse solution for example returns coefficients that best approximate the true mapping function.

An alternative expression for polynomial mapping of degree N, where degree is the maximum sum of powers of u and v coordinates, is $$X(u, v) = x = \sum_{i=0}^{N} \sum_{j=0}^{N-i} a_{i,j} u^i v^j$$

$$Y(u, v) = y = \sum_{i=0}^{N} \sum_{j=0}^{N-i} b_{i,j} u^i v^j$$

When N=1, the mapping reduces to the previously described affine transformation, for which three anchor-point correspondences need be established:

$$x = a_{00} + a_{10}u + a_{01}v$$

$$y = b_{00} + b_{10}u + b_{01}v$$

When the anchor objects cover the full image area, the polynomial transformations given above are low-order global mapping functions operating over the entire image. For this kind of non-linear mapping uses more anchor points than the linear mappings, the spatial correspondence of the mapped objects with respect to the imaged structures will be better than for the linear mapping outlined before.

Given the computed mapping coefficients, point objects will map to points, however generally at a floating-point position in the target image. Line objects are mapped to polynomial shapes in general. Therefore, to retain the rectilinear shape of line objects in the target image, lines may be defined on the basis of points, which are mapped according to the mapping functions X(u,v),Y(u,v), and a line object must subsequently be redrawn in the target image based on the mapped points.

1.2.3. Thin Plate Spline Mapping

When the number of anchor points is larger than needed to compute the transformation, an over-determined system of equation results. The solution coefficients are such that the mapped anchor points will not exactly coincide with their corresponding anchor points in the target image, but will fit them in the least squares sense for example.

An exact interpolation of the target anchor points can be achieved however by adding a corrective non-linear term to the linear affine mapping functions:

$$x = a_0 + a_1 u + a_2 v + \sum_{j=1}^{N} c_j U(r_j)$$

$$y = b_0 + b_1 u + b_2 v + \sum_{j=1}^{N} c_j U(r_j)$$

The first terms represent the necessary affine portion of the mapping, as introduced and computed previously from the N anchor point correspondences, the last term represents the radial basis function $U(r) = r^2 \log r^2$ with $r_j^2 = (u-u_j)^2 + (v-v_j)^2$. The N anchor points $(u_j, v_j)$ are called the control points and may be placed in an arbitrary (non-rectangular) manner over the image.

2. Expression and Location of Geometrical Objects in the Anchor Object Model

The model anchor objects are used to define a coordinate system in which the geometrical objects are referenced. In principle any model objects may serve this purpose, but typically objects that are easy to map will be used. In the context of the present invention, an anchor point set or an anchor line set are suitable objects.

Euclidean Coordinates and Euclidean Object Mappings Based on a Line Segment

Two points a and b of a point set containing at least two points may be chosen to attach a local model coordinate system to. The x axis may be chosen to coincide with the line connecting both points. The sense may be chosen from the first point towards the second, and the length of the segment ab may be normalized to unity. The direction of the y axis may be chosen to be perpendicular to the x axis, and the sense of the y axis is such that a right-handed coordinate system is formed with the x-axis (rotation from positive x axis to positive y axis in the counterclockwise direction). In this way an orthonormal coordinate system is formed, which is suitable for use in Euclidean object mappings.

Barycentric Coordinates and Affine Object Mappings Based on a Triangle

Figure 3:
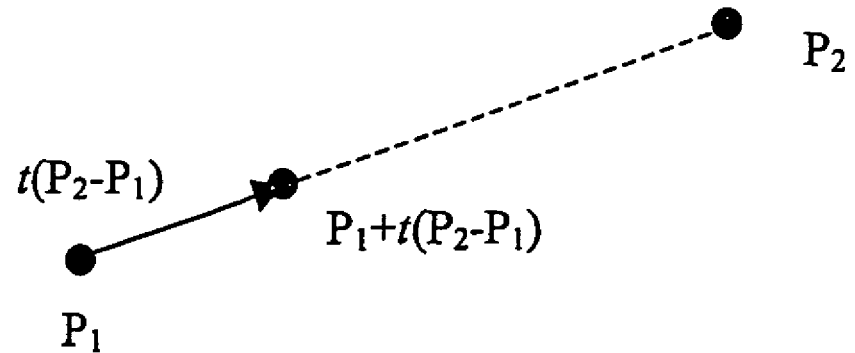
FIG. 3. Barycentric coordinates: (a) affine combination of two points, (b) affine combination of three points.
Figure 3:
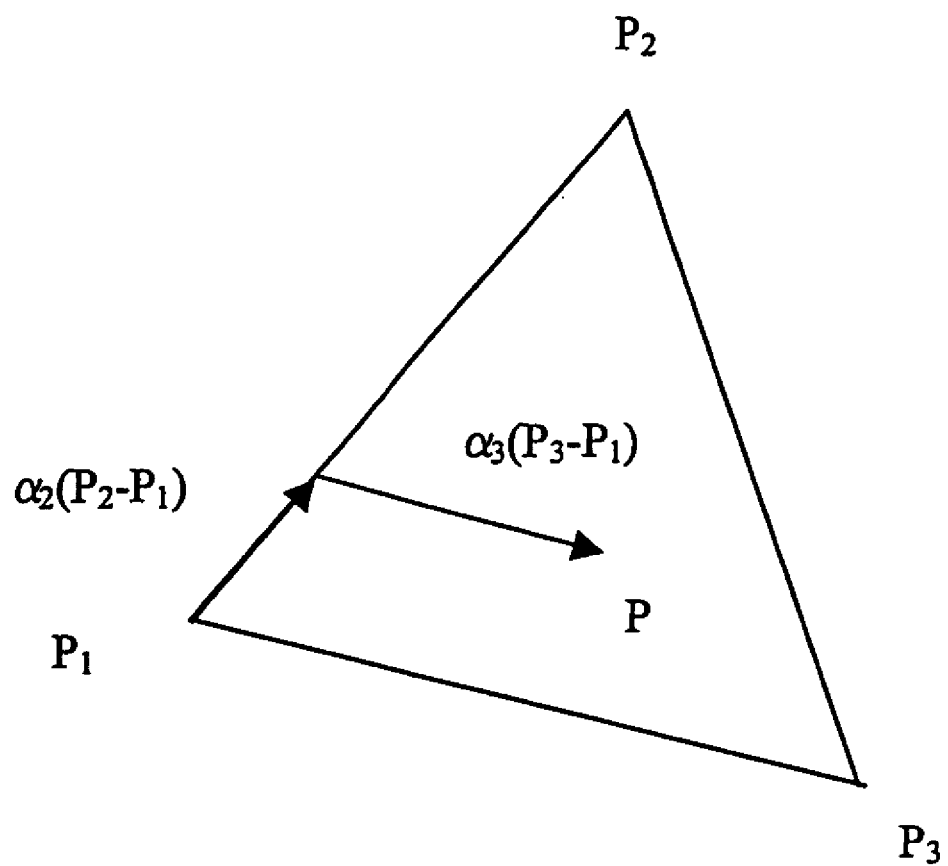

An affine combination of two points $P_1$ and $P_2$ is defined as $P = \alpha_1 P_1 + \alpha_2 P_2$ with $\alpha_1 + \alpha_2 = 1$. This point P lies somewhere on the line segment joining $P_1$ and $P_2$ if $0 \leq t \leq 1$. An equivalent form, $P = (1-t)P_1 + tP_2 = P_1 + t(P_2 - P_1)$ is an affine transformation with $a_2 = t$. If any $\alpha_i$ is less than zero or greater than one, then the point will lie outside the line segment. If either $\alpha_1$ or $\alpha_2$ is zero, then the point will coincide with either $P_2$ or $P_1$ respectively (FIG. 3 (a)) Similarly, a new point P in a plane can be defined by as a combination of three points $P_1, P_2, P_3$ defined as $P = \alpha_1 P_1 + \alpha_2 P_2 + \alpha_3 P_3$ with $\alpha_1 + \alpha_2 + \alpha_3 = 1$. This affine combination defines a point in the triangle $\Delta P_1 P_2 P_3$ as $P = P_1 + \alpha_2(P_2 - P_1) + \alpha_3(P_3 - P_1)$. If any $\alpha_i$ is less than zero or greater than one, then the point will lie outside the triangle. If any $\alpha_i$ is zero, then the point will lie on the boundary of the triangle (FIG. 3 (b)).

A coordinate frame for affine n-space or shortly frame, which describes the positions of points in the affine plane (n=2), is now formed by choosing an origin point 0 and two linearly independent vectors. In two dimensions this frame is denoted $(\vec{v}_1, \vec{v}_2, O)$. Any point P can be written uniquely as $P = p_1 \vec{v}_1 + p_2 \vec{v}_2 + O$. If we define points $P_0, P_1, P_2$ by $P_0 = O, P_1 = O + \vec{v}_1, P_2 = O + \vec{v}_2$ and define $p_0$ to be $p_0 = 1 - (p_1 + p_2)$, then P can be equivalently be written as $P = p_0 P_0 + p_1 P_1 + p_2 P_2$, whereby $p_0 + p_1 + p_2 = 1$ In this form, the values $(p_0, p_1, p_2)$ are called the barycentric coordinates of P relative to the points $(P_0, P_1, P_2)$, and are used to describe objects in an affine coordinate frame based on a triple of points forming a triangle $\Delta P_0 P_1 P_2$. The vectors $(\vec{v}_1, \vec{v}_2)$ obviously represent the sides $P_1 - P_0 = \vec{v}_1$ and $P_2 - P_0 = \vec{v}_2$ respectively of the triangle $\Delta P_0 P_1 P_2$.

Two frames $(v_1, v_2, O)$ and $(\vec{v}_1', \vec{v}_2', O')$ formed by two triples of points can be related to each other, that is the coordinates of a point object in one frame can be converted to coordinates of a mapped point in the other frame by expressing the vectors and origin of the first frame in terms of the basis vectors and origin of the second frame since the latter form a basis for the space of vectors. Thus the change of coordinates is accomplished via a matrix multiplication. The rows of the matrix consist of the coordinates of the vectors of the old (first) frame F relative to the new (second) frame F, and is denotes as follows $$p_1 \vec{v}_1 + p_2 \vec{v}_2 + O = \begin{bmatrix} p_1 & p_2 & 1 \end{bmatrix} \begin{bmatrix} \vec{v}_1 \\ \vec{v}_2 \\ O \end{bmatrix}$$

$$= \begin{bmatrix} p_1 & p_2 & 1 \end{bmatrix} \begin{bmatrix} e_{11} & e_{12} & 0 \\ e_{21} & e_{22} & 0 \\ e_{31} & e_{32} & 1 \end{bmatrix} \begin{bmatrix} \vec{v}_1' \\ \vec{v}_2' \\ O' \end{bmatrix}$$

$$= \begin{bmatrix} p_1 & p_2 & 1 \end{bmatrix} E \begin{bmatrix} \vec{v}_1' \\ \vec{v}_2' \\ O' \end{bmatrix}$$

and first two terms of the product $$\begin{bmatrix} p_1 & p_2 & 1 \end{bmatrix} \begin{bmatrix} e_{11} & e_{12} & 0 \\ e_{21} & e_{22} & 0 \\ e_{31} & e_{32} & 1 \end{bmatrix}$$

represent the new coordinates in the frame $(\vec{v}_1', \vec{v}_2', O')$. For any of the vectors of the first frame, their coordinates in the second frame, and hence their associated row in the matrix E are computed by projecting the vector of the first frame on each basis vector of the second frame. Let $\vec{t}$ represent a general vector in the target frame $(\vec{v}_1', \vec{v}_2', O')$. If we define $$proj_{\vec{t}}(\vec{v}_1') = \frac{(\vec{t} \cdot \vec{v}_1')}{|\vec{v}_1'|^2} \vec{v}_1' = p_1' \vec{v}_1'$$

$$proj_{\vec{t}}(\vec{v}_2') = \frac{(\vec{t} \cdot \vec{v}_2')}{|\vec{v}_2'|^2} \vec{v}_2' = p_2' \vec{v}_2'$$

then $p_1', p_2'$ represents the coordinates of $\vec{t}$ in $(\vec{v}_1', \vec{v}_2', O')$. By letting $\vec{t} = \vec{v}_1$, the quantities $p_1', p_2'$ represent $e_{11}$ and $e_{12}$, likewise by letting $\vec{t} = \vec{v}_2$, the quantities $p_1', p_2'$ represent $e_{21}$ and $e_{22}$. By letting $\vec{t} = O' - O$, $e_3$, and $e_{32}$ are calculated.

In three dimensions, the matrix E that relates a frame $(\vec{v}_1, \vec{v}_2, \vec{v}_3, O)$ with a frame $(\vec{v}_1', \vec{v}_2', \vec{v}_3', O')$ is 4×4 matrix, and is computed using Cramer's rule by defining the determinants $$D = \vec{v}_1' \cdot (\vec{v}_2' \times \vec{v}_3') = \begin{vmatrix} v_{11}' & v_{12}' & v_{13}' \\ v_{21}' & v_{22}' & v_{23}' \\ v_{31}' & v_{32}' & v_{33}' \end{vmatrix}$$

$$D_t = \vec{t} \cdot (\vec{v}_2' \times \vec{v}_3') = \begin{vmatrix} t_1 & t_2 & t_3 \\ v_{21}' & v_{22}' & v_{23}' \\ v_{31}' & v_{32}' & v_{33}' \end{vmatrix}$$

$$D_2 = \vec{v}_1' \cdot (\vec{t} \times \vec{v}_3') = \begin{vmatrix} v_{11}' & v_{12}' & v_{13}' \\ t_1 & t_2 & t_3 \\ v_{31}' & v_{32}' & v_{33}' \end{vmatrix}$$

$$D_3 = \vec{v}_1' \cdot (\vec{v}_2' \times \vec{t}) = \begin{vmatrix} v_{11}' & v_{12}' & v_{13}' \\ v_{21}' & v_{22}' & v_{23}' \\ t_1 & t_2 & t_3 \end{vmatrix}$$

and calculating $$p_1' = \frac{D_1}{D}, p_2' = \frac{D_2}{D}, p_3' = \frac{D_3}{D},$$

which represent the coordinates of $\vec{t}$ in $(\vec{v}_1', \vec{v}_2', \vec{v}_3', O')$. By letting $\vec{t} = \vec{v}_1$, $\vec{t} = \vec{t}_2$, $\vec{t} = \vec{v}_3$, $\vec{t} = O' - O$, the four rows of E are computed.

Obviously, the first frame represent the coordinate system formed by the anchor point in the model image, the second frame represents the coordinate system formed by the mapped anchor points in the actual image, and the conversion describes the way objects defined in the model coordinate frame map to their corresponding objects in the actual image.

This affine mapping method can be extended to include vectors as well. Let $\vec{v}$ be a vector in a first affine frame, and let P and Q be any two points such that $\vec{v} = P - Q$. We define the mapped vector by an affine transformation F into the second frame to be the vector given by $F(\vec{v}) = F(P-Q) = F(P) - F(O)$.

A line can be defined as the combination of a point and a vector, $L = P + \alpha \vec{v}$, and the mapping of a line object is determined by $F(L) = F(P) + \alpha F(\vec{v})$.

Projective Coordinates and Object Mappings Based on a Quadrangle

Similarly as a point may be uniquely expressed with barycentric coordinates in an affine frame based on a triangle, a point may be uniquely expressed in coordinates defined by a projective frame based on a quadrangle. A geometric and an algebraic procedure to map a point referenced with respect to a projective frame in the model image towards its corresponding points in the projective frame of the target image are outlined in the sequel.

Geometric Procedure

Similar to the preservation of ratio of distances and the rule of three in affine or bilinear coordinate mappings, the projective mapping preserves the cross ratio of distances between four collinear points. The procedure further relies on the fact that the intersection point of parallel lines maps under a projective transform to the vanishing point for that line direction.

The cross ratio $Cr(p_1,p_2;p_3,p_4)$ of four collinear points $p_1,p_2,p_3,p_4$ in the projective plane (with their counterpart points $P_1,P_2,P_3,P_4$ in the affine plane) is given by $$Cr(P_1, P_2; P_3, P_4) = \frac{\frac{\Delta_{13}}{\Delta_{23}}}{\frac{\Delta_{14}}{\Delta_{24}}} = \frac{\Delta_{13}\Delta_{24}}{\Delta_{23}\Delta_{14}}$$

in which $\Delta_{ij}$ is the Euclidean distance between points $P_i$ and $P_j$ with affine coordinates $(x_i,y_i)$ resp. $(x_j,y_j)$. The Euclidean distance $\Delta_{ij}$ is computed from the homogeneous coordinates $(X_i,Y_i,W_i)$ and $(X_j,Y_j,W_j)$ of the projective points $p_i$ and $p_j$ as $$\Delta_{ij} = \sqrt{\left(\frac{X_i}{W_i} - \frac{X_j}{W_j}\right)^2 + \left(\frac{Y_i}{W_i} - \frac{Y_j}{W_j}\right)^2}$$

If one of the points lies at infinity, the terms in $Cr(p_1,p_2;p_3,p_4)$ cancel and the cross ratio reduces to the ratio of the remaining three points.

Figure 4:
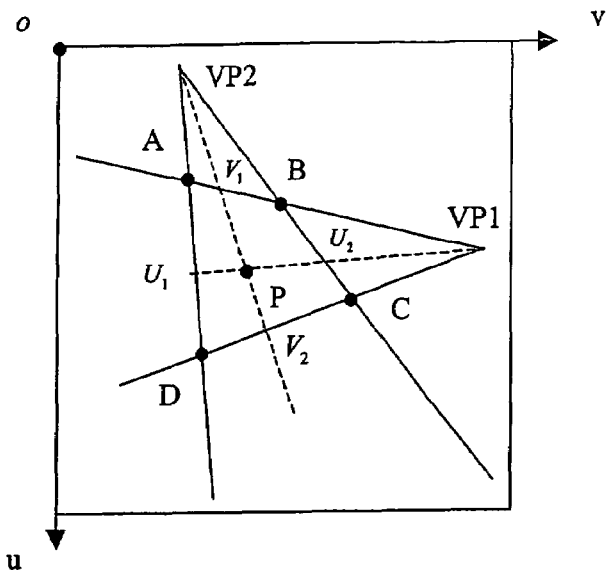
FIG. 4. Projective mapping of a point P referenced in a quadrangle ABCD to a point P' referenced in a quadrangle A'B' C'D'.
Figure 4:
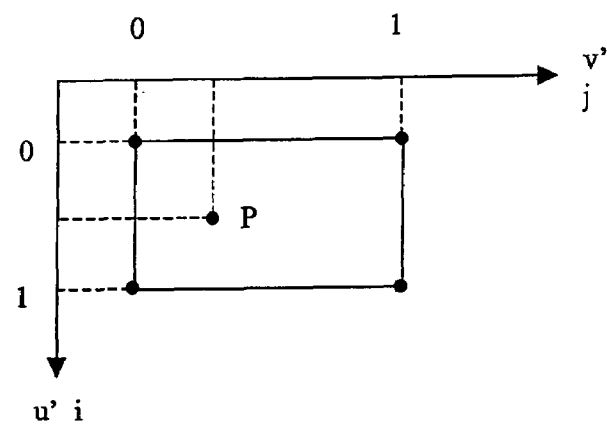
Figure 4:
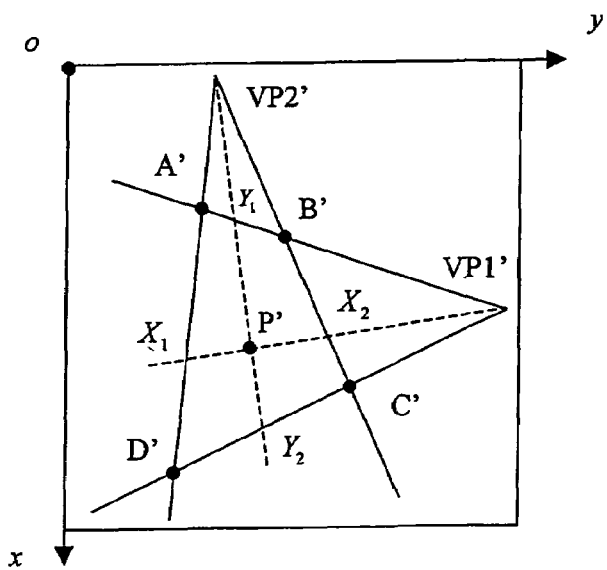

Referring to FIG. 4, the projective j coordinate in the unit square reference frame is computed from the affine collinear points $U_1,P,U_2,VP_1$ in the model quadrangle as $$j = 1 - \frac{1}{Cr(U_1, P; U_2, VP_1)}.$$

The projective coordinate in the unit square reference frame is computed from the affine collinear points $V_2,V_1,P,VP_2$ in a similar way.

The mapped point P' is now obtained as the intersection of line $X_1VP_1'$ (or equivalently $X_1X_2$) and line $Y_2VP_2'$ (or equivalently $Y_1Y_2$). The point $Y_2$ (and similarly $Y_1$), that is the mapping of point $V_2$, is constructed by drawing it on line D'C' at a distance from point D' towards C' such that the cross ratio of the resulting configuration $Cr(D',Y_2;C',VP_1)$ in the target image is equal to the cross ratio $Cr(U_1,P;U_2,VP_1)$ in the model, which cross ratio is equivalent to the cross ratio $1/(1-j)$ based on the projective coordinate j. The point $X_1$ and $X_2$ are similarly constructed using the cross ratio based on the projective coordinate i.

Algebraic Procedure

The algebraic procedure to determine the projective mapping of the model point referenced with respect to a model quadrangle is based on the projective transformation T established from the correspondences of the four quadrangle corner points as outlined previously. The homogeneous coordinates of the position of the mapped input point in the target image are straightforwardly obtained by multiplying the projective coordinates of P with T. The image coordinates of P' are subsequently obtained by dividing by the homogeneous coordinate, that is $$x = \frac{a_{11}u + a_{12}v + a_{13}}{a_{31}u + a_{32}v + a_{33}}$$
$$y = \frac{a_{21}u + a_{22}v + a_{23}}{a_{31}u + a_{32}v + a_{33}}.$$

3. Mapping of Geometrical Objects 3.1. Application of the Mapping Function to the Geometrical Objects' Defining Parameters Objects that are defined in the local coordinate system are now mapped using the computed transform into the output image. In the sequel, the mapping result is described for some elementary, frequently used, geometric objects. The linear projective mapping is of particular interest because of its invariance properties w.r.t. the shape of the mapped object.

Point Mapping

Points are fundamental geometric objects because they can be used in a direct way to describe anatomical locations, or in an indirect way to specify higher dimensional objects such as lines and circles. Given a transform T specified by establishing a correspondence between anchor objects in model and target image as outlined before, a model point u=(u,v) is mapped into a point x=(x,y) in the target image by applying the transform, i.e. x=Tu.

Line Mapping

Lines remain lines under an Euclidean (similarity) transform, an affine and a projective transform. Under a bilinear transform, however, lines remain only straight if they are parallel with the image coordinate axes, otherwise they are transformed into curves of second degree (parabolas).

Rectangle, Polygons and Region of Interest (ROI) Mapping and ROI Extracting

A polygon is made up of a set of piecewise linear borders, hence it remains a polygon under an Euclidean (similarity) transform, an affine and a projective transform. Of special interest is a rectangle for it may represent a region of interest in the image. Rectangles remain only rectangular under an Euclidean similarity transform. An affine transform will deform a rectangle into a parallelogram, since parallelism is preserved. A projective transform deforms a rectangle generally into a quadrangle. In the sequel a method is devised to map rectangles under an Euclidean, affine or projective mapping that preserves the target shape of a rectangle.

A rectangular ROI may be encoded in a coordinate system (u',v') resp. (x',y') defined by the first two model anchor points as depicted in FIG. 1. Two types of encoding are discerned, and are termed relative or absolute in the context of the present invention.

Relative encoding is the term introduced to denote that two points, defining the base of the rectangular ROI, together with the height of the ROI are specified to determine the ROI. ROI's parallel to the image borders in the (u,v) model coordinate system will generally map to ROI's non-parallel to the image borders in the (x,y) target coordinate system. Hence, due to the rotation component, the borders of the resulting mapped ROI will not stay parallel to the original model ROI's borders.

This kind of relative mapping is advantageous for e.g. bone age scoring, where the rotation of the fingers must be taken into account when extracting a rectangular ROI, such that the bone axis in the resulting extracted ROI is parallel to the ROI's image border.

Absolute encoding is the term introduced to denote that only one base point, defining the origin of the rectangular ROI, together with the width and height of the ROI are specified to determine the ROI. The rotation component is left out in this kind of ROI mapping. ROIs parallel to the image borders in the (u,v) model coordinate system will map to ROIs also parallel to the image borders in the (x,y) target coordinate system. Hence, due to neglecting the rotation component, the borders of the resulting mapped ROI will always stay parallel to the original model ROIs' borders.

This kind of absolute mapping is advantageous for extracting ROI's at full resolution in e.g. a full leg examination to allow for better positional accuracy during placing the measurement points. These ROIs typically comprise regions along the femoral and tibial shaft, and regions in the femoral neck area, knee joint area, and ankle joint area. Irrespective of the actual bone axis angle, the user typically wishes to extract a ROI that stays parallel to the target image borders. Hence, the rotation that is implied from the transformation matrix must be ignored. This can be achieved by only mapping the ROI's origin by applying the transformation matrix to the ROI's origin in the model, and further leaving the angle of the model ROI fixed. The drawing of the rectangle is then completed in one of two ways. Width and height of the mapping rectangle are determined from the scale factor of the decomposed transformation matrix, and the rectangle is drawn such that parallellness to the model rectangle is retained. An alternative is to map the diagonally juxtaposed ROI corner point by applying the transformation to it and further complete the ROI drawing, respecting equal angles (i.e. parallellness) of the corresponding model and target ROI sides.

Polygonal objects may be mapped in similar congruent way, either relatively or absolutely. Relative mapping is achieved by mapping a base line and constructing the remainder of the sides, and further applying the scale factor to the length of the sides and respecting the inter-side angles of the polygon. Absolute mapping is achieved by mapping the polygon's origin point, and redraw the polygon applying the scale factor to the sides' lengths but leaving the sides parallel with the corresponding model polygon sides.

The encoding of a rectangular or polygonal ROI in the model image proceeds as follows (FIG. 1). The u' component of the (u',v') coordinates of the base points of the rectangular or polygonal ROI are determined by calculating the speed with respect to the anchor line formed by anchor points $a_1$ and $a_2$. The speed of a point with respect to line a $a_2$ is equal to the relative projected distance from the origin of the (u',v') coordinate system along the u' axis. The origin of the (u',v') coordinates coincides with the anchor point $a_1$. A projected point coinciding with $a_1$ has speed 0 (such point lies on the v' axis). A projected point coinciding with $a_2$ has speed 1. Any point projecting between $a_1$ and $a_2$ has speed between 0 and 1, any point projecting before $a_1$ has speed less than 0, any point projecting after $a_2$ has speed greater than 1. The length between $a_1$ and $a_2$ is thus normed to unity. This length also norms the v' coordinate. The v' axis is constructed perpendicular onto the u' axis and has a positive sense such that it forms a right-handed coordinate system. The v' coordinate of a point is determined by projecting the point onto the v' axis and dividing the projected distance to the origin with the length between a, and $a_2$.

In the relative encoding, both base points of rectangular region are encoded in this way, along with the height of the rectangle. In the absolute encoding, only one base point is encoded, along with width and height of the rectangle.

From a small number of anchor point correspondences, the geometric transformation is computed, and applied to the base point(s) of the model rectangle.

In the relative case, the scale factor that is applied to width and height may be determined from the ratio of the distance between the mapped rectangle's base points to the distance between the model rectangle's base points.

In the absolute case, the scale factor that is applied to width and height is determined by first decomposing the affine or projective mapping matrix into its elementary geometric operations of scaling, translation, rotation, sharing and perspective components as derived previously, and secondly taking the scale factor from the scaling matrix. This absolute mapping ignores the rotation component in the geometric transformation, by concatenating only scaling, translation, sharing (for the affine mapping) and perspective (for the projective mapping) components.

The absolute angle ROI mapping and ROI extracting has the obvious advantage that the ROI stays aligned with the target image coordinate axes x and y, such that the spatial interpolation to extract the ROI may operate in a separable way along rows and columns.

Circle and Ellipse Mapping

A circle remains a circle under an Euclidean (similarity) transform. The circle's center maps as a point as described before, the radius is scaled with a scale factor S as determined before.

Under an projective or affine transform, a circle is projected into a conic or a separate kind of conic, the ellipse, hyperbola and parabola object, the parameters of which can be determined from the transform coefficients as described in the sequel.

The general equation of a circle in the model is given by $$(u-u_0)^2+(v-v_0)^2=r^2$$

Writing the projective transform T that maps (u,v) model points into (x,y) target points as $$\begin{bmatrix} x \\ y \\ 1 \end{bmatrix} = \begin{bmatrix} a & b & c \\ d & e & f \\ g & h & i \end{bmatrix} \begin{bmatrix} u \\ v \\ 1 \end{bmatrix}$$

wherein the coefficient i may be normalized to 1 since the transform s is only determined up to a scale factor. The equation that relates (u,v) to (x,y) is then given by applying the inverse transform $T^{-1}$, which yields $$\begin{bmatrix} u \\ v \\ 1 \end{bmatrix} = \begin{bmatrix} ei-fh & ch-bi & bf-ce \\ fg-di & ai-cg & cd-af \\ dh-eg & bg-ah & ae-bd \end{bmatrix} \begin{bmatrix} x \\ y \\ 1 \end{bmatrix} = \begin{bmatrix} A' & B' & C' \\ D' & E' & F' \\ G' & H' & I' \end{bmatrix} \begin{bmatrix} x \\ y \\ 1 \end{bmatrix}$$

For the pure affine case for which g=h=0, the (u,v) to (x,y) relationship simplifies into $$\begin{bmatrix} u \\ v \\ 1 \end{bmatrix} = \begin{bmatrix} e & -b & bf-ce \\ -d & a & cd-af \\ 0 & 0 & ae-bd \end{bmatrix} \begin{bmatrix} x \\ y \\ 1 \end{bmatrix} = \begin{bmatrix} A'' & B'' & C'' \\ D'' & E'' & F'' \\ G'' & H'' & I'' \end{bmatrix} \begin{bmatrix} x \\ y \\ 1 \end{bmatrix}$$

Introducing this projective resp. affine equation into the equation of the circle yields a quadric equation of the mapped object in the target image, which is the general equation of a conic in two dimensions $$Ax^2 + 2Bxy + Cy^2 + 2Dx + 2Ey + F = 0$$

Or written in matrix form $$[x\ y\ 1] Q \begin{bmatrix} x \\ y \\ 1 \end{bmatrix} \text{ with } Q = \begin{bmatrix} A & B & D \\ B & C & E \\ D & E & F \end{bmatrix},$$

in which the coefficients A . . . F are a function of the original coefficients a . . . h of the transformation matrix T, established by correspondence.

The conic is a real ellipse object when det(Q)<0 and AC−B²>0. The ellipse's major axis makes an angle α with the x axis given by $$\tan(2\alpha) = \frac{2B}{A-C}$$

In a similar way as a circle object, an ellipse object maps to a conic object under an Euclidean, affine or projective mapping.

Bézier and Spline Object Mapping

These objects are mapped in the image by first transforming their control points and secondly regenerating the curve (or surface in is 3D) according to the object's new control points. Bézier and spline curves remain invariant under affine mapping, and rational Bézier and rational spline curves remain invariant under projective mapping, that is, the transformed curve can be obtained by regenerating the curve solely on the basis of the transformed control points. In the sequel the definition of each curve is given along with its mapped form.

Bézier Curve

More specifically, an nth-degree Bézier curve is defined as $$C(u) = \sum_{i=0}^{n} B_{i,n}(u) P_i \quad 0 \le u \le 1$$

The basis blending functions are the nth-degree Bernstein polynomials given by $$B_{i,n}(u) = \frac{n!}{i!(n-i)!} u^i (1-u)^{n-i}.$$

The geometric coefficients $\{P_i\}$ in this formula are called the control points For plane curves, $P_i=(x_i,y_i)$, for space curves $P_i=(x_i,y_i,z_i)$. Denoting by the set $\{P_i'\}$ the mapped control points obtained by applying the geometric mapping to the original set $\{P_i\}$, the mapped nth-degree Bézier curve C'(u) is generated on the basis of the mapped control points, i.e.

$$C'(u) = \sum_{i=0}^{n} B_{i,n}(u) P_i' \quad 0 \le u \le 1$$

Rational Bézier Curve

An nth-degree rational Bézier curve is defined as $$C(u) = \frac{\sum_{i=0}^{n} B_{i,n}(u) w_i P_i}{\sum_{i=0}^{n} B_{i,n}(u) w_i} = \sum_{i=0}^{n} R_{i,n}(u) P_i \quad 0 \le u \le 1$$

where $$R_{i,n}(u) = \frac{B_{i,n}(u) w_i}{\sum_{j=0}^{n} B_{j,n}(u) w_j}$$

represent the rational basis functions for this curve form. Similar to the mapping of polynomial Bézier curves, the mapped rational Bézier curve is obtained through a geometric transformation of the control points, i.e.

$$C'(u) = \sum_{i=0}^{n} R_{i,n}(u) P_i' \quad 0 \le u \le 1$$

The underlying idea for using rational curves is that a rational curve in n-dimensional space can be represented as a polynomial non-rational Bézier curve in (n+1)-dimensional space by introducing homogeneous coordinates, the homogeneous coordinate W(u), by which the other coordinates X(u),Y(u) (for 2D curves) or X(u),Y(u),Z(u) (for 3D curves) are divided, being $$W(u) = \sum_{j=0}^{n} B_{j,n}(u) w_j$$

This operation of division by the homogeneous coordinate geometrically corresponds to a perspective map on the hyper-plane W=1 with the center at the origin. In X-ray imaging the origin physically represents the X-ray point source, the hyper-plane W=1 represents the detector plane. This operation is advantageous in that some important curves such as circles, ellipses, hyperbolas, cylinders, cones, spheres cannot be represented by polynomials, but can be represented using the rational functions, which are the ratio of polynomials.

In the context of radiographic and medical imaging, this operation may be used to derive an analytic representation for the projection of a 3D space curve in the patient onto the detector or imaging plane. Another example is in the field of digital radiograph reconstruction (DRR) from a CT image, where the shape of a curvilinear object in the CT image, possibly fitted to 3D data points, can be represented as rational Bézier curve, and its projection in the DRR obtained by homogenizing the 3D curve. To apply the projection directly, the curvilinear object must be represented in the coordinate system with the z-axis positively oriented from the X-ray source towards the detector plane, and being perpendicular to it. The function z(u), representing the depth or height w.r.t. the origin along the curve in 3D space, will now act as the homogeneous coordinate W(u), and will be used as the denominator to obtain the projection of the space curve onto the detector plane. The functions x(u),y(u) of the object in 3D space represent the homogeneous coordinates X(u),Y(u). The location (x'(u),y'(u)) of the projected 3D curve in the 2D image on the detector plane is then obtained as $$x'(u) = \frac{X(u)}{W(u)}, y'(u) = \frac{Y(u)}{W(u)}$$

Therefore the use and representation of 3D object shapes by rational Bézier curves has a physical ground in the imaging process. When the object is not represented in a coordinate system with z-axis aligned with the central projection direction, a rigid object transformation, represented by an Euclidean transformation as outlined above, must first be applied onto the control points of x(u),y(u),z(u) (equivalently a 4×4 matrix may be applied to the four-dimensional control points expressed in homogeneous coordinates).

Spline Curve

Because Bézier curves that are only represented by one polynomial segment are inadequate to represent object shapes with high geometric detail (requiring a high degree) and because a change in shape affects all control points, spline curves have been introduced that allow local control of the object shape yet efficient representation.

A p-th degree B-spline curve is defined as $$C(u) = \sum_{i=0}^{n} N_{i,p}(u) P_i \quad a \le u \le b$$

where the $\{P_i\}$ represent the control points jointly forming the control polygon, and the $\{N_{i,p}(u)\}$ are the p-th degree basis spline (B-spline) basis functions defined on the non-periodic and non-uniform knot vector (m+1 knots) of non-decreasing real numbers and with multiplicity p+1 of a and b $$U = \{u_0, \ldots u_m\} = \{a, \ldots a, u_{p+1}, \ldots u_{m-p-1}, b, \ldots b\}$$

A spline curve with no interior knots is a Bézier curve. Such spline curve has a knot vector of the form U={0, . . . , 0, 1, . . . 1} with multiplicity p+1 of 0 and 1, yielding the Bernstein polynomials of degree p.

Similar to the mapping of Bézier curves, the mapped spline curve can be obtained by mapping the control points $\{P_i\}$ and regenerating the spline curve in the target image on the basis of the mapped control points $\{P_i'\}$ $$C'(u) = \sum_{i=0}^{n} N_{i,p}(u) P_i' \quad a \le u \le b$$

Rational Spline Curve

A p-th degree rational spline curve is defined as $$C(u) = \frac{\sum_{i=0}^{n} N_{i,p}(u) w_i P_i}{\sum_{i=0}^{n} N_{i,p}(u) w_i} = \sum_{i=0}^{n} R_{i,p}(u) P_i \quad a \le u \le b \text{ with}$$

$$R_{i,p}(u) = \frac{N_{i,p}(u) w_i}{\sum_{j=0}^{n} N_{j,p}(u) w_j}$$

Again, the $\{P_i\}$ represent the control points jointly forming the control polygon, and $\{w_i\}$ are the weights. When the knot vector is non-periodic and non-uniform, i.e.

$$U = \{u_0, \ldots u_m\} = \{a, \ldots a, u_{p+1}, \ldots u_{m-p-1}, b, \ldots b\}$$

with multiplicity p+1 of a and b, these curves are known in the prior art as NURBS curves (Non-Uniform Rational Basic Splines). A NURBS curve with no interior knots is a rational Bézier curve. In general, NURBS curves comprise non-rational B-splines and non-rational and rational Bézier curve as special cases.

As with rational Bézier curves, all transformations and orthographic projections of C(u) can be obtained by applying the operation to the three-dimensional control points $\{P_i\}$. This property is called affine invariance. When perspective transformations are applied are applied to curves, new weights $\{w_i\}$ must be computed within the formalism of NURBS representation, which property is called invariance under perspective transformations.

Bézier and spline objects are particularly useful to represent the outlines of diagnostic areas in medical images, an instantiated model of which needs to be mapped into the actual image prior to applying a deformation algorithm to obtain the actual segmentation. This mapping operation is needed in applications such as segmenting a bone on a musculoskeletal image based on deformable contour models,
determining the lung field outlines on a thorax image or
determining the breast skin line on a mammographic image.

Compound Geometric Object Mapping

Compound geometric objects are objects that are composed of elementary objects such as line segments, circular arcs and polynomial shapes. The mapping of compound objects is achieved by mapping each of the constituent objects in turn. Examples of compound geometric objects in the field of medical imaging are the outlines of prostheses and implants used in the course of planning a joint replacement in orthopedics or the outlines of screw plates and cages used in planning traumatologic surgery.

Figure 5:
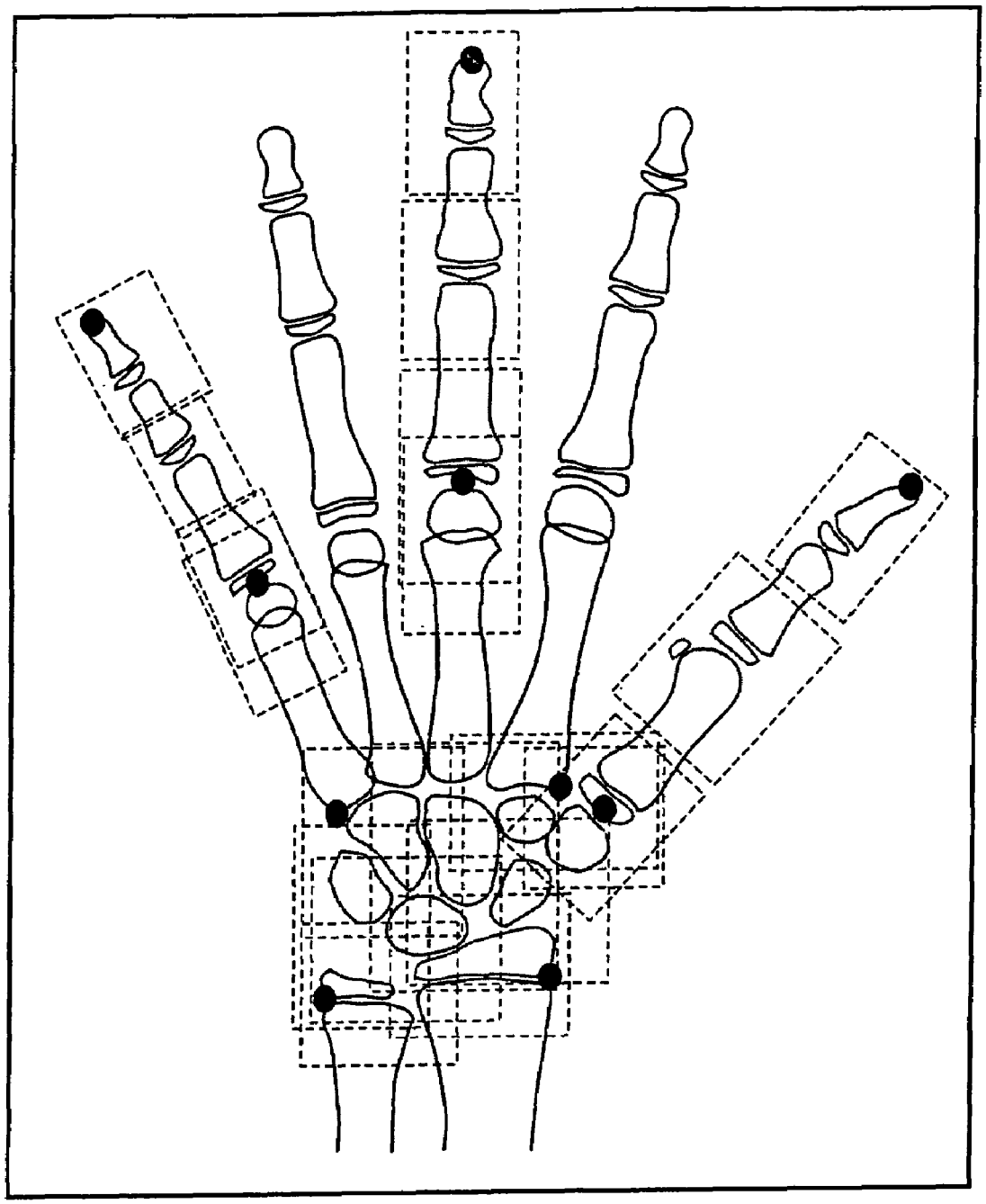
FIG. 5. Regions of interest in a hand examination encoded according to a relative encoding. The ROI's mapped from the model template towards the target image will be aligned with the actual bone axes in the image. The anchor points (FIG. 5 (a)), taken in pairs, determine the phalangeal and metacarpal ROI's (FIG. 5 (b)); a quadruple of anchor points (FIG. 5 (a)) determines the carpal ROI's (FIG. 5 (c)) in this example.
Figure 6:
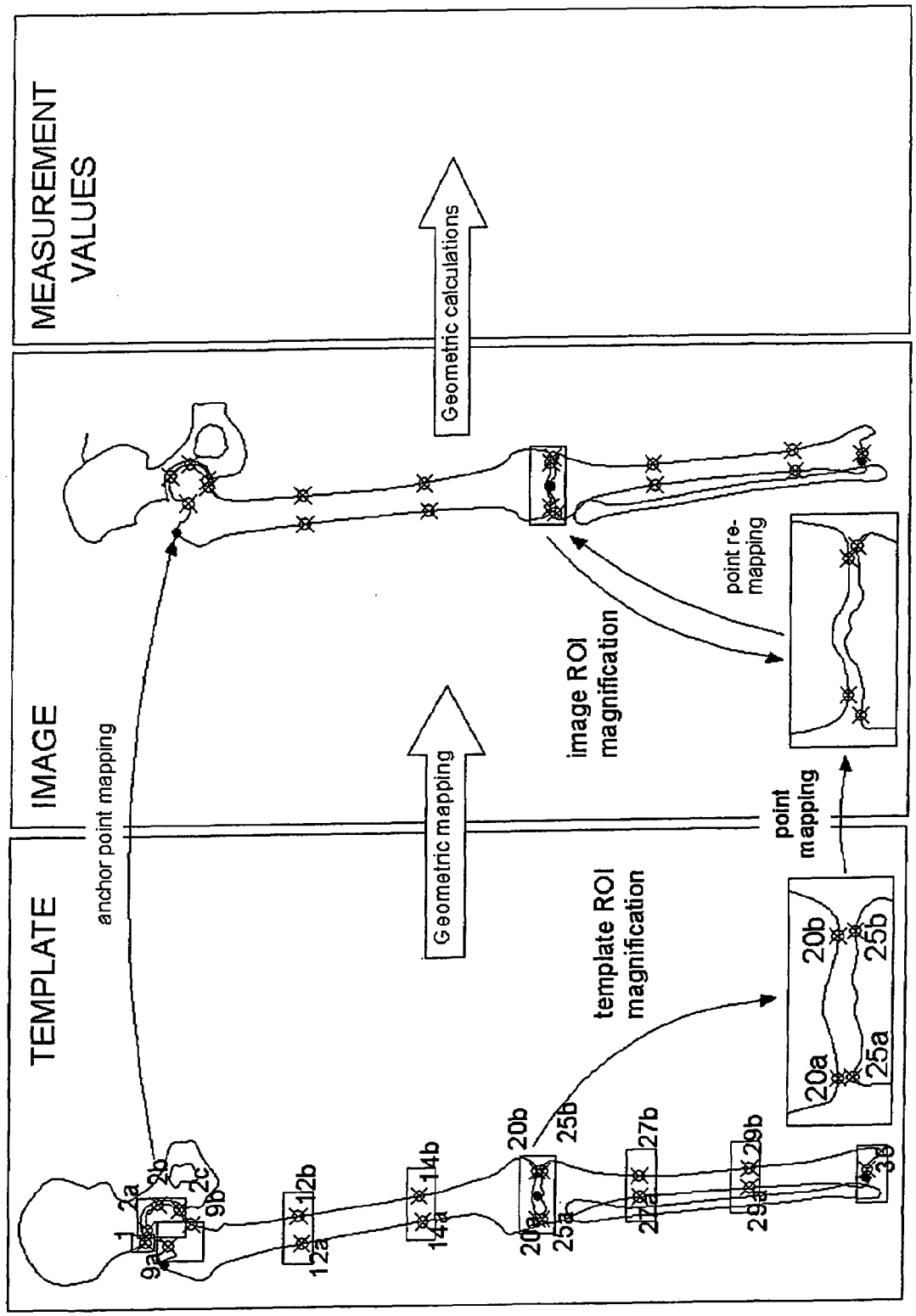
FIG. 6. Regions of interest in a full-leg examination, encoded according to an absolute encoding. The ROI's mapped from the model template towards the target image remain aligned with the image borders. The anchor points are the top of the greater trochanter, the center of the knee joint and the center of the ankle joint (black rounds in the template pane). Greater trochanter and center of knee serve to determine the femoral neck and femoral shaft as well as the knee joint ROI's in this example. Center of knee and center of ankle serve to determine the tibial shaft as well as the knee joint and ankle joint ROI's in this example.
Figure 7:
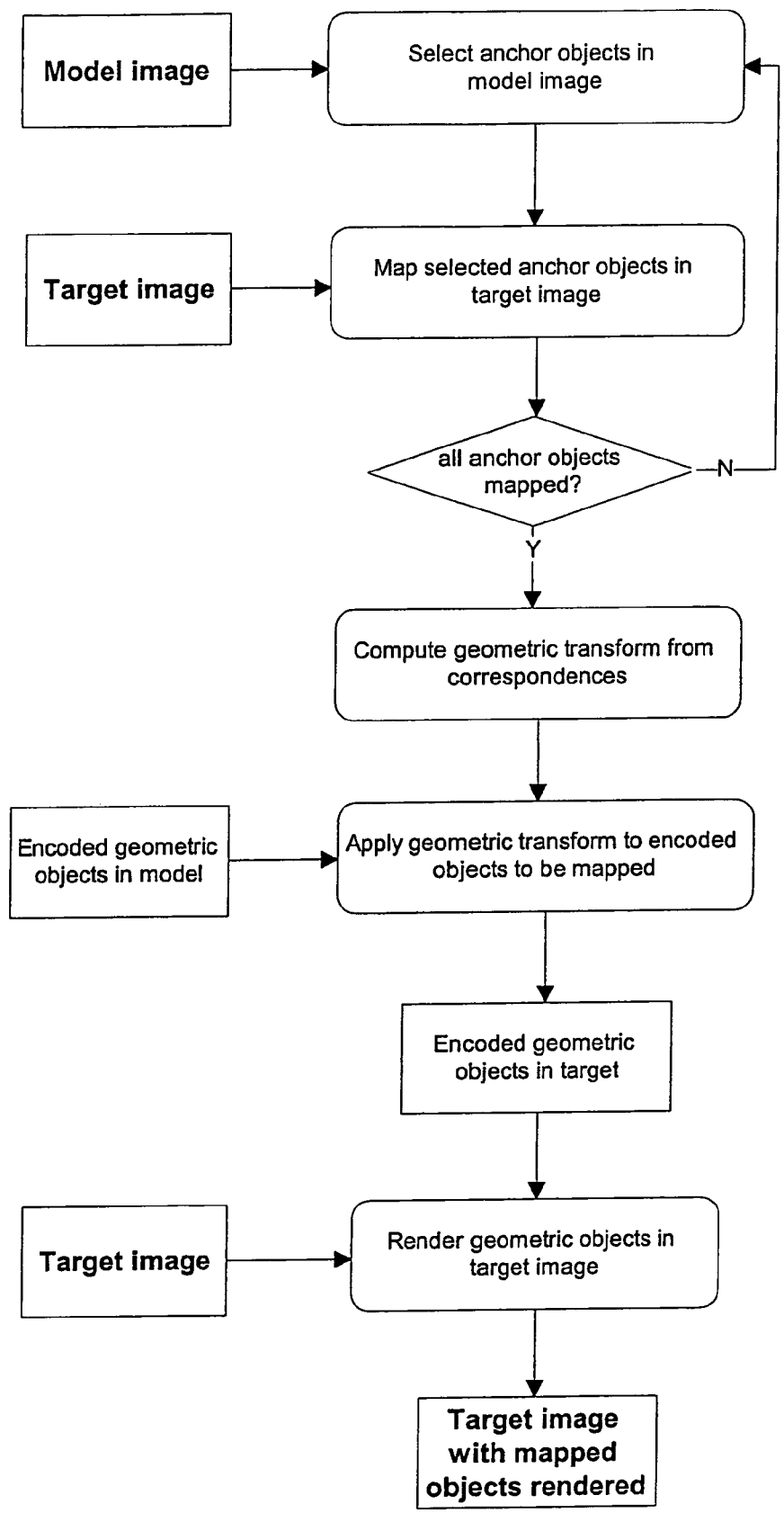
FIG. 7. General system overview of mapping geometric objects in images by means of anchor objects.

3.2 Engine and User Interface (FIG. 5 and FIG. 6 (a))

The system that implements the geometric mapping method consists of two parts.

The engine refers to the internal part that is responsible for the chaining of the mapping of anchor points, internal computation of the geometric transformation, the expression and encoding of the geometric objects with respect to the model and target coordinate systems, the application of the geometric transformation to the objects' defining parameters and the regeneration of the objects' graphical outline in the target image. The chaining of the anchor point mapping may be based on a dependency graph of the kind that is disclosed in European patent application EP A 1 349 098 for the mapping of measurement points. Anchor objects and depending geometric objects are represented as internal objects instantiated from classes, the design and implementation of which adhere to the principles of object-oriented systems.

Depending on the application, which will be disclosed in the sequel, the engine is further responsible for additional tasks. For example, in the case of ROI mapping and extraction, these tasks comprise image re-sampling and interpolation, image memory management, and database operations.

The user interface constitutes the external part of the system and will typically consist of two windows. The first window shows the model objects in geometric relationship to their anchor objects. The second window normally represents the window into which the model objects must be mapped; this window will typically comprise an image. The user interface comprises means to manipulate the position of the anchor objects in the target image with e.g. a mouse cursor, upon which the mapped geometric objects are repainted according to their new pose.

In a specific embodiment the first window showing the model objects may be omitted and may be represented by a list of model anchor objects. These model anchor objects are selected successively from the list prior to mapping them in the target image.

The system will basically operate in two modes.

In an interactive mode, the user sequentially selects the model objects e.g. by clicking on them. A copy of this model object may now be attached to the cursor, and the user is prompted to map this model object into the actual image.

For point anchor points, the user will drag and drop each point on the intended anatomical location in conformance with the model image. The system will warn the user when a sufficient number of points is reached to compute the geometric transform. When too few points are input than needed, the system may issue a warning that the transform is underdetermined.

Anchor line objects may be defined by two points, and after selection of the model line, each of its defining points is positioned in a similar way as for individual anchor points. These points serve as handles in the image when the line's position and orientation needs be adjusted.

When the required number of anchor points or anchor lines is reached to compute the geometric transform, the system calculates the mapping between the model object coordinate system and the image object coordinate system. Finally, the model objects are mapped from the model image into the actual image by applying the geometric transform to their defining parameters.

Readjusting any of the anchor points in the actual image, will invoke a re-computation of the geometric transform, and will accordingly update the position of the geometric objects by applying the new transform to the objects' defining parameters.

In an automatic mode, the system highlights each of the model anchor objects in turn according to the chaining that is imposed on them in a dependency graph, so as to hint the user to map them in the image, and subsequently maps each of the objects that is defined in the coordinate system defined by the model anchor objects. The positioning in this mode is further enhanced in that an initial position of the subsequent points may determined on the basis of previous points, e.g. the initial position of the third point in over-determined Euclidean mapping may be computed on the basis of the first two (which define an Euclidean mapping in a determined way), and the fourth point's position may be determined based on the mapped position of the former three, and so on.

Both the interactive and automatic mode has the advantage that no wrong correspondence can be established. When e.g. a model quadrangle ABCD has to be mapped onto a target quadrangle A'B' C'D' the order of mapping each constituent object is imposed either by the user or by the system. Due to the labeling of the objects, at any time, it is known which object of the model is being mapped. This method of operation is therefore invariant against permutations of the objects to be mapped.

3.3 Application of the Object Mapping Methods

Radiological Scoring (FIG. 5)

The current invention is particularly useful in computer-assisted radiological scoring. In a preferred embodiment, a set of image ROIs is extracted and each ROI is juxtaposed against a set of the references images, while at the same time scrolling through them so as to find the best matching reference stage. This principle, disclosed in European patent application EP A 1 293 925, may be applied to e.g. bone age scoring, where a fixed number of pre-defined skeletal sites need be staged against a set of reference images. The anchor point objects, useful to reference and locate all skeletal RUS and carpal ROIs in the Tanner and Whitehouse method, are e.g. the distal tip of the distal phalanx and the midpoint of the proximal phalanx-metacarpal joint of fingers III and V (4 points), the distal tip of the distal phalanx and the proximal midpoint of the metacarpal of the thumb (2 points), the proximal midpoints of the metacarpals II and V (two points) and the distal midpoints of the ulna and radius (two points), a total of 8 anchor points. These points, depicted in FIG. 5 (*a*) are used in pairs to map ROI's from a model template into the image using the methods of Euclidean similarity mapping outlined above. Each pair establishes the transform matrix that is used to map the ROIs of the model image into the target image. Subsequently, each ROI is extracted from the image by a re-sampling and interpolation process such as bilinear or bi-cubic spline interpolation, before it is finally placed in close vicinity with the scoring reference pictures and reference items. A schematic of the ROI images is shown in FIG. 5 (*b*) for the RUS bones, and FIG. 5 (*c*) for the carpal bones.

Instead of extracting ROIs from the image to be scored and presenting them in juxtaposed to the reference pictures, an second embodiment, that uses the spatial mapping operation based on anchor points, consists in mapping the reference pictures into the image, in close vicinity to the skeletal region (e.g. in a touching manner to the ROI of a particular region). Using the scroll wheel of the mouse, or the up and down keys of the keypad, the reference pictures are scrolled through, and the user selects that reference stage corresponding to the largest similarity between reference picture and skeletal region. This manner of operation has the advantage that the full input image remains visible to the user.

The ROI and reference picture mapping is further advantageous in a third embodiment based on registration where similarity is measured by pixel-wise comparison based on correlation. In this embodiment the reference picture is mapped into the image in a spatially coinciding manner so as to overlay on the corresponding skeletal site. The anchor points with respect to which the skeletal regions are referenced are used to superimpose the reference picture onto the skeletal region to be scored. A linear or non-linear image registration operation is applied to the ROI to find its most corresponding position with respect to the skeletal site and the degree of similarity of the registration is recorded. This registration operation is repeated for each of the reference pictures, and that stage is selected for which the degree of similarity is the highest.

Radiological Image Quality Control

The current invention is further particular useful in the context of quality control and quality assurance by means of an analyzing phantom. A phantom typically consist of a spatial arrangement of analyzing objects with fixed topological layout to measure system and image quality parameters such as SNR, MTF, DQE, contrast and geometric resolution. The image data analysis that is carried out to compute these parameters operates on specific imaged phantom locations. To determine for example the contrast of circular disks with respect to a background, the disk area (i.e. some region fully contained within the disk border), and the surrounding background of the disk must be sampled. The spatial location of these samples may be defined in an analysis object model (based on a CAD model of the phantom) that is mapped into the target image (the image of the phantom). The phantom comprises a small number of easily discernible and locatable marker points that serve as anchor points with respect to which all analyzing objects are referenced. The image of these anchor points are located by the user and brought into correspondence with their model anchor points. A mapping transformation is computed, and the positions of all analyzing points in the image of the phantom are next computed. The intensity at the analyzing points' positions is finally used to compute the quality measures. For example, to evaluate the local contrast in the image, the difference of intensity in a mapped circular region inside a disk and a mapped annular concentric region around said disk is computed.

Radiological Image Measurements (FIG. 6)

The current invention is also useful to alleviate the burden of pre-positioning key measurement points in a radiological measurement application such as disclosed in European patent application EP A 1 349 098. A plurality of measurement points in this application must be mapped into the image onto their corresponding anatomical location. Three placement modes are disclosed in this patent: manual placement, ROI magnified placement and automated placement based on deformable contour segmentation.

The process of the first placement mode is enhanced by attaching a measurement point to the cursor and pre-mapping it in the target image onto a location that is obtained by applying the established geometric transform to each model measurement point of the measurement template. Anchor points are used to establish the geometric transform, however also measurement points themselves may be used to refine, actualize or compute the transformation on the fly as the points' positions become available in the course of executing the measurement template.

The second placement mode is speeded up by the current invention by first auto-zooming the ROI that comprises a measurement point to a larger or full resolution, and secondly by pre-mapping the measurement points towards an initial position in close vicinity to their true anatomical position. The auto-zooming step magnifies a particular portion of the image either in a separate popped-up window, of in a manner so as to completely fill the current image window. The pre-mapping step maps a specific measurement point towards its initial position in its associated ROI; the user accomplishes the mapping task by dragging the point towards its final position in said magnified ROI. The coordinates of the point in the original image are finally computed by applying the inverse geometric transform that links the coordinate system of the zoomed ROI with that of the original image. Both ROI selection and measurement point mapping are based on the methods of anchor object correspondence and geometric transformation computation and application outlined above.

The third placement mode does not require any user intervention as to the placement of the measurement points. Instead, the position of measurement points and objects is specified indirectly using their associated position and local geometric and photometric features on an instantiated and subsequently deformed model contour. The initial pose (rotation, translation and scale) of the instantiated model contour is based on a small set of anchor objects, the correspondence of which with the target anchor objects establishes the mapping transform.

Particularly when performing 3D measurement templates according to European patent application EP A 1 349 098, defined as a plurality of individual measurement templates associated with specific slices in a 3D image and displayed as a stack in the template window, measurement points must be placed on their corresponding position of the corresponding slice in the actual 3D image. High-resolution 3D image of current modalities such as MR or CT typically comprise 1000 slices. It is obvious that, during executing the measurement session, it is a laborious task to scroll through the stack of slices until the correct slice is found onto which the measurement point must be positioned. By using a geometric transformation established by correspondence of a few number of landmark anchor points in model and actual 3D image, the number of slices to scroll through can be narrowed down to a range specific to the measurement point, thereby reducing the search time. For the transformation is three dimensional, not only a initial slice is pre-selected when mapping a point, it is also pre-positioned within a slice. After having selected the target slice, the point is further positioned within the slice by dragging it onto its associated anatomical position. The 3D coordinates of all measurement points are subsequently used to compute 3D metric entities such as distances and angles.

Orthopedic and Traumatologic Implant Templating

Instead of mapping atomic geometric objects such as points, lines, circles and splines, objects composed of such elementary objects may be mapped as a whole from a model image window into the target image, solely on the basis of a small number of anchor points, by applying the mapping transformation to each of the constituent elementary objects. Such composed objects are typically implant or prosthesis outlines obtained directly from a prosthesis manufacturer as a 2D or 3D CAD model or from vectorized scanned contours of a conventional 2D acetate template. This mapping considerably speeds up the selection and placement of the prosthesis, a process commonly known as templating. When performed on film or on a computer display as the non-automated computer equivalent of manual film templating, it requires extensive manipulation of the objects, such as successive translations and rotations in a non-systematic manner so as to have a fit of the prosthesis outline with the anatomic image data. The current invention is particularly suited to aid in the positioning process by providing an initial position that may coincide well with the particular imaged patient anatomy, the accuracy of which depends on the positional accuracy of the anchor points or objects and the accuracy with which the template is defined in the coordinate system of the anchor objects.

There is also a positional dependency of template objects that may be used to automate the placement of further objects. In total hip replacement, the planning comprises the selection and placement of typically three components of an implant: a femoral stem, a femoral head and an acetabular cup. When the femoral stem is first placed in the radiographic image, the placement of the femoral head, which mechanically fits onto the stem, may be auto-placed, using the femoral stem as the anchor object, such that the axis of the head coincides with the femoral neck axis of the femoral template component. Likewise the acetabular cup is auto-placed by a mapping that now uses the femoral head as the anchor object: the translational component follows from the position of the femoral head center and it remains to apply a suitable rotation to the cup. When the acetabular cup is first placed, its center and orientation serve to determine the preposition and—orientation of the femoral head, which in turn determine the preposition and—orientation of the femoral stem.

Another application that is related to prosthesis templating is in the field of traumatology, where the planning of surgical procedures requires the placement of graphical models of screw cages onto the image. Also here, this placement may be speeded up and made more accurate when the graphical models are linked to and made dependent on the prior placement of anchor points or anchor objects. Whenever the position of the ancestor objects is known, they are used as anchor objects to which the depending objects are referred and pre-positioned by the mapping methods as described in the above.

Radiological Image Segmentation

The current invention is also useful in the field image segmentation. For medical images, this basic image processing operation aims at delineating anatomic structures and organs, in order to perform e.g. planimetric, perimeter, area or volumetric measurements. For this purpose, graphic models are used that initialize the outline of the object(s) to be segmented. These contours are subsequently deformed by applying image-internal (e.g. gradients) and contour-internal (e.g. local curvature) forces, an approach known in the prior art as snakes segmentation. However, an important problem involves the pre-positioning of the model contours. By defining the contour(s) in the coordinate system of a small number of anchor objects (e.g anatomical landmark points), the contour(s)' initial position in the target image can be computed by applying the established geometric transformation to the contour's defining parameters. For example, a polygonal outline can be mapped by applying the transformation to the polygon's vertices; a spline outline can be mapped by applying the transformation to the spline's control points. In either example, the initial contour outline in the target image is generated on the basis of the defining parameters. Examples of applications of segmentation are given in the sequel.

In the field of mammography, computer-aided diagnosis algorithms must operate in the image on the breast mass region only; hence a segmentation of the skin line is needed. A mapping of an initial model contour may be based on characteristic points describing the breast outline. In particular, the following anchor points may be used in affinely warping a model outline towards an initial breast skin outline: (a) in the CC (cranio-caudal) mammographic view: nipple, left and right point of the breast image near the chest wall; (b) in the MLO (medio-lateral oblique) view: base of the pectoral muscle at the chest wall, the outermost position of the pectoral muscle at the top of the breast image, the nipple and the bottom of breast image near the chest wall. The mapped initial contour is further deformed according to e.g. snakes approach, until it coincides with the actual 'breast mass'-to-'direct exposure region' boundary in the mammogram.

Similar region delineation is needed in the computer-assisted diagnosis of thorax images, where the extent of lung fields need be determined. The mapping of lung field outlines here may be based on characteristic points in a thorax image. In particular, the following anchor points may be used in affinely or projectively mapping a model outline towards an initial lung field outline: left and right costophrenic sulcus (also called the costophrenic angles, each angle formed between the inner surface of the ribs and the dome of the diaphragm), left and right intersection of the heart shadow with the dome of the diaphragm, and left and right lower clavicle-"rib three" intersection points.

I claim:

1. A method of mapping a geometric object of a model image in a digital target image comprising
    selecting at least one anchor point of the geometric object in the model image,
    mapping the anchor point into said target image to obtain a target anchor point,
    computing a linear geometric transformation matrix on the basis of correspondence between the at least one anchor point and the corresponding target anchor point,
    decomposing the linear geometric transformation matrix in a sequence of elementary geometric operations selected from translations, scalings, rotations, shearings and projectivities, wherein each of the elementary geometric operations is represented by a matrix,
    canceling at least one elementary geometric operation associated with a selected or small component by equating the matrix associated with said selected or small component to a corresponding identity matrix,
    recombining the resulting sequence of matrices of elementary operations into a transformation matrix, and
    applying the geometric transformation corresponding with the resulting transformation matrix to the model geometric object to map said model geometric object to a corresponding mapped position in said target image.

2. The method according to claim 1 wherein the model is displayed as a model image comprising anchor objects.

3. The method according to claim 2, wherein the anchor objects are points.

4. The method according to claim 2, wherein the anchor objects are lines.

5. The method according to claim 2 wherein geometric objects are rendered in the model image.

6. The method according to claim 5 wherein the geometric objects are encoded relative to the anchor objects.

7. The method according to claim 5, wherein the anchor objects or the geometrical objects represent anatomic entities.

8. The method according to claim 1, wherein the target image is a medical image.

* * * * *